US009574184B2

(12) United States Patent
Grabowski et al.

(10) Patent No.: US 9,574,184 B2
(45) Date of Patent: Feb. 21, 2017

(54) LYSOSOMAL PROTEIN TARGETING SEQUENCE AND THERAPEUTIC APPLICATIONS OF SAME

(71) Applicant: Children's Hospital Medical Center, Cincinnati, OH (US)

(72) Inventors: Gregory A. Grabowski, Lexington, MA (US); Benjamin Liou, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 320 days.

(21) Appl. No.: 14/494,065

(22) Filed: Sep. 23, 2014

(65) Prior Publication Data
US 2016/0237414 A1 Aug. 18, 2016

Related U.S. Application Data

(60) Provisional application No. 61/882,272, filed on Sep. 25, 2013.

(51) Int. Cl.
*C12N 9/24* (2006.01)
*A61K 38/00* (2006.01)
(52) U.S. Cl.
CPC ..... *C12N 9/2402* (2013.01); *C12Y 302/01045* (2013.01); *A61K 38/00* (2013.01)
(58) Field of Classification Search
None
See application file for complete search history.

(56) References Cited

U.S. PATENT DOCUMENTS

2009/0239807 A1* 9/2009 Horowitz .............. A61K 38/07
514/1.1

OTHER PUBLICATIONS

Lavaut (Blood Cells, Molecules, and Diseases 46 (2011) 327).*
Achord, DT, et al., "Human beta-glucuronidase: in vivo clearance and in vitro uptake by a glycoprotein recognition system on reticuloendothelial cells," *Cell*, 1978, 15:269-278, 10 pgs.
Altschul, SF, et al., "Basic local alignment search tool," *J. Mol. Biol.*, 1990, 215(3): 403-410, 8 pgs.
Altschul, SF et al., "[27] Local alignment statistics," *Methods in Enzymology*, 1996, 1 266:460-480, 21 pgs.
Altschul, SF, et al., "Gapped BLAST and PSI-BLAST: a new generation of protein database search programs", *Nucleic Acids Res.* 1997, 25:3389-3402, 14 pgs.
Barriocanal, JG, et al., "Biosynthesis, glycosylation, movement throught the golgi system and transport to lysosomes by N-linked carbohydrate independent mechanism of three lysosomal integral membrane proteins," *J Biol Chem.* 1986, 261(35):16755-16763, 9 pgs.
Barton, NW, et al., "Dose-dependent responses to macrophage-targeted glucocerebrosidase in a child with Gaucher disease," *J.Pediatr.* 1992, 120:277-280, 4 pgs.
Baxevanis, AD, ed., et al., *Bioinformatics: A Practical Guide to the Analysis of Genes and Proteins*, John Wiley & Sons, New York, NY, 1998, 2 pgs.
Berg-Fussman A, et al., "Human Acid beta-glucosidase: N-glycosylation site occupancy and the effect of glycosylation on enzymatic activity," *J Biol Chem.* 1993, 268(20):14861-66, 6 pgs.
Blanz J, et al., "Disease-causing mutations within the lysosomal integral membrane protein type 2 (LIMP-2) reveal the nature of binding to its ligand beta-glucocerebrosidase," *Hum Mol Genet.* 2010, 19(4):563-72, 10 pgs.
Brady RO, et al., "Metabolism of glucocerebrosides; II. Evidence of an enzymatic deficiency in Gaucher's disease," *Biochem Biophys Res Commun.* 1965, 18(2):221-5, 5 pgs.
Brady RO, et al., "Demonstration of a deficiency of glucocerebroside-cleaving enzyme in Gaucher's disease," *Journal of Clinical Investigation.* 1966, 45(7):1112-5, 4 pgs.
Braulke, T., Ph.D., et al., "138: I-Cell Disease and Pseudo-Hurler Polydystrophy: Disorders of Lysosomal Enzyme Phosphorylation and Localization," In: Scriver CR, Beaudet, A., Sly, W. and Valle, D. ed. *The Metabolic & Molecular Bases of Inherited Disease.* New York: McGraw-Hill; 2001, Abstract only, 6 pgs.
Brumshtein, B., et al. "Structural comparison of differently glycosylated forms of acid-beta-glucosidase, the defective enzyme in Gaucher disease." Acta Crystallogr Section D, Biol Crystallogr, 2006, D62(Pt 12):1458-1465, 8 pgs.
Bultron G, et al., "The risk of Parkinson's disease in type 1 Gaucher disease," *Journal of Inherited Metabolic Disease.* 2010, 33(2):167-73, 11 pgs.
Chen P, et al., "Molecular determinants of enterovirus 71 viral entry: cleft around GLN-172 on VP1 protein interacts with variable region on scavenge receptor B 2," *The Journal of Biological Chemistiy.* 2012, 287(9):6406-20, 15 pgs.
Cullen V, et al., "Acid beta-glucosidase mutants linked to Gaucher disease, Parkinson disease, and Lewy body dementia alter alpha-synuclein processing," *Ann Neurol.* 2011, 69(6):940-53, 14 pgs.
Deduve, C., "Lysosomes revisited," *Eur.J.Biochem.* 1983, 137:391-397, 7 pgs.
Desnick, R.J., et al., "alpha-N-Acetylgalactosaminidase deficiency: Schindler Disease," In *The Metabolic Basis of Inherited Disease.* C.R. Scriver, A.L. Beaudet, W.S. Sly, and D. Valle, editors. New York: McGraw-Hill. 1989, p. 1751-1796, Abstract only 2 pgs.
Desnick, R.J., et al. "alpha-Galactosidase A Deficiency: Fabry Disease," In *The Metabolic & Molecular Bases of Inherited Disease.* C.R. Scriver, Beaudet, A., Sly, W. and Valle, D., editors. New York: McGraw-Hill, 2001, p. 3733-3774, Abstract only 2 pgs.
Edgar RC, "MUSCLE: a multiple sequence alignment method with reduced time and space complexity," *BMC Bioinformatics.* 2004, 5:113, 19 pgs.

(Continued)

*Primary Examiner* — Suzanne M Noakes
*Assistant Examiner* — Jae W Lee
(74) *Attorney, Agent, or Firm* — Frost Brown Todd LLC

(57) ABSTRACT

The present disclosure relates to methods of treating diseases states such as lysosomal storage diseases and/or neurodegenerative diseases. Also disclosed are one or more compositions that may be useful for one or more of the disclosed methods, including compositions that may comprise acid β-glucosidase (GCase) protein comprising one or more mutations, peptides of acid β-glucosidase, and DNA vectors and cell lines related to acid β-glucosidase peptides or proteins.

15 Claims, 22 Drawing Sheets

(56) References Cited

OTHER PUBLICATIONS

Edgar RC, "MUSCLE: multiple sequence alignment with high accuracy and high throughput," *Nucleic Acids Res.* 2004, 32(5):1792-97, 6 pgs.
Ezkowitz AB, et al., "Molecular characterization of the human macrophage mannose receptor: Demonstration of multiple carbohydrate recognition-like domains and phagocytosis of yeasts in Cos-1 cells," *J Exp Med.* 1990, 172:1785-94, 10 pgs.
Fabbro D, et al., "Human acid beta-glucosidase. Use of inhibitory and activating monoclonal antibodies to investigate the enzyme's catalytic mechanism and saposin A and C binding sites," J Biol Chem. 1991, 266(23):15021-27, 7 pgs.
Goldstein, J.L., et al., "Role of lysosomal acid lipase in the metabolism of plasma low density lipoprotein," *J. Biol. Chem.* 1975, 250(21):8487-8795, 10 pgs.
Gough NR, et al., "Utilization of the indirect lysosome targeting pathway by lysosome-associated membrane proteins (LAMPs) is influenced largely by the C-terminal residue of their GYXXphi targeting signals," *J Cell Science.* 1999, 112:4257-69, 13 pgs.
Grabowski GA, et al., "Part 16: Lysosomal Disorders; Chapter 146.1: Gaucher Disease: Phenotypic and Genetic Variation," In: Scriver C, Beaudet, A., Sly, W., and Valle, D. ed. *The Metabolic and Molecular Bases of Inherited Diseases.* New York: McGraw-Hill; 2006, 51 pgs.
Grabowski GA, et al., "Part 16 Lysomol Disorders; Chaper 146: Gaucher Disease," In: Valle D, Beaudet, A.L., Vogelstein, B., Kinzler, K.W., Antonarakis, S.E., Ballabio, A., Sly, W.S. ed. *The Metabolic and Molecular Bases of Inherited Disease.* New York: McGraw-Hill; 2010, 141 pgs.
Grabowski, G.A., et al., "Gaucher disease: A prototype for molecular medicine," *Crit.Rev.Hem.Onco.* 1996, 23:25-55, 31 pgs.
Horton, J.D., et al., "SREBPs: activators of the complete program of cholesterol and fatty acid synthesis in the liver," *J Clin Invest* 2002, 109(9):1125-1131, 7 pgs.
Kaplan, A., et al., "Phosphohexosyl components of a lysosomal enzyme are recognized by pinocytosis receptors on human fibroblasts," *Proc.Natl.Acad.Sci.USA*, 1977, 74:2026-2030, 5 pgs.
Knipper M, et al. "Deafness in LIMP2-deficient mice due to early loss of the potassium channel KCNQ1/KCNE1 in marginal cells of the stria vascularis," *The Journal of Physiology.* 2006, 576(Pt 1):73-86, 14 pgs.
Kornfeld S., "Structure and function of the mannose 6-phosphate/ insulin like growth factor II receptors," *AnnuRevBiochem.* 1992, 61:307-30, 26 pgs.
Leonova T, et al., "Fate and sorting of acid beta-glucosidase in transgenic mammalian cells," *Mol Genet Metab.* 2000, 70(4):281-94, 14 pgs.
Liou B, et al., "Is E326K glucocerebrosidase a polymorphic or pathological variant?" *Molecular Genetics and Metabolism.* 2012, 105(3):528-9, 2 pgs.
Liou B, et al., "Analyses of variant acid beta-glucosidases: Effects of Gaucher disease mutations," *The Journal of Biological Chemistry.* 2006, 281(7):4242-53, 13 pgs.
Lopez G, et al., "Predicting parkinsonism: new opportunities from Gaucher disease," *Molecular Genetics and Metabolism.* 2013, 109(3):235-6, 2 pgs.
Maniwang E, et al., "Is Parkinson disease associated with lysosomal integral membrane protein type-2?: Challenges in interpreting association data," *Molecular Genetics and Metabolism.* 2013, 108(4):269-71, 3 pgs.
Mazzulli JR, et al., "Gaucher disease glucocerebrosidase and alpha-synuclein form a bidirectional pathogenic loop in synucleinopathies," *Cell.* 2011;146(1):37-52, 16 pgs.
Misener, S, Ed. et al., *Bioinformatics Methods and Protocols* (Methods in Molecular Biology, vol. 132), Humana Press, 1999, 6 pgs.
Misra S, et al., "Structural basis for acidic-cluster-dileucine sorting-signal recognition by VHS domains," *Nature.* 2002, 415:933-7, 5 pgs.
Mullin NP, et al., "Mechanism of $Ca^{2+}$ and monosaccharide binding to a C-type carbohydrate-recognition domain of the macrophage mannose receptor," *J Biol Chem.* 1997, 272(9):5668-81, 15 pgs.
Nichols, W.C., et al., "Mutations in GBA are associated with familial Parkinson disease susceptibility and age at onset," *Neurology* 2009, 72:310-316, 7 pgs.
Ogata S, et al., "Lysosomal targeting of Limp II membrane glycoprotein requires a novel Leu-Ile motif at a particular position in its cytoplasmic tail," *The Journal of Biological Chemistry.* 1994, 269(7):5210-17, 8 pgs.
Reczek D, et al., "LIMP-2 is a receptor for lysosomal mannose-6-phosphate-independent targeting of beta-glucocerebrosidase," *Cell.* 2007, 131(4):770-83, 14 pgs.
Reitman, ML, et al., "Lysosomal enzyme targeting: N-acetylglucosaminyl-phosphotransferase selectively phosphorylated native lysosomal enzymes," J. Biol. Chem. 1981, 256(23):11977-11980, 4 pgs.
Saftig P, et al., "Lysosome biogenesis and lysosomal membrane proteins: trafficking meets function," *Nature Reviews Molecular Cell Biology.* 2009, 10(9):623-35, 13 pgs.
Saftig P, et al., "Lysosomal membrane proteins: life between acid and neutral conditions," *Biochemical Society Transactions.* 2010, 38(6):1420-3, 4 pgs.
Sardi SP, et al., "CNS expression of glucocerebrosidase corrects alpha-synuclein pathology and memory in a mouse model of Gaucher-related synucleinopathy," *Proc Natl Acad Sci USA.* 2011, 108(29):12101-6, 6 pgs.
Sardi SP, et al., "Augmenting CNS glucocerebrosidase activity as a therapeutic strategy for parkinsonism and other Gaucher-related synucleinopathies," *Proc Natl Acad Sci USA.* 2013, 110(9):3537-42, 6 pgs.
Sardi SP, et al., "Mutant GBA1 expression and synucleinopathy risk: first insights from cellular and mouse models," *Neuro-Degenerative Diseases.* 2012, 10(1-4):195-202, Abstract only 1, pg.
Sidransky E, et al. "Multicenter analysis of glucocerebrosidase mutations in Parkinson's disease," *The New England Journal of Medicine.* 2009, 361(17):1651-61, 11 pgs.
Sidransky, E., "Gaucher disease and parkinsonism," *Mol Genet Metab* 2005, 84:302-304, 3 pgs.
Sorge J, et al., "Molecular cloning and nucleotide sequence of the human glucocerebrosidase gene," *ProcNatlAcadSciUSA.* 1985, 82:7289-93, 6 pgs.
Sun Y, et al., "Saposin C is required for normal resistance of acid beta-glucosidase to proteolytic degradation," *J Biol Chem.* 2003, 278(34):31918-23, 7 pgs.
Velayati A, et al., "A mutation in SCARB2 is a modifier in Gaucher disease," *Human Mutation.* 2011, 32(11):1232-38, 7 pgs.
Wang X, et al., "A sensor-adaptor mechanism for enterovirus uncoating from structures of EV71," *Nature Structural & Molecular Biology.* 2012, 19(4):424-29, 17 pgs.
Westbroek W, et al., "Exploring the link between glucocerebrosidase mutations and parkinsonism," *Trends in Molecular Medicine.* 2011, 17(9):485-93, 9 pgs.
Yamayoshi S, et al., "Identification of a human SCARB2 region that is important for enterovirus 71 binding and infection," *Journal of Virology.* 2011, 85(10):4937-46, 10 pgs.
Yamayoshi S, et al., "Scavenger receptor B2 is a cellular receptor for enterovirus 71," *Nature Medicine.* 2009, 15(7):798-801, 5 pgs.
Zachos C, et al., "A critical histidine residue within LIMP-2 mediates pH sensitive binding to its ligand beta-glucocerebrosidase," *Traffic.* 2012, 13(8):1113-23, 11 pgs.

\* cited by examiner

FIG 3

```
ARPCIPKSFG.YSSVVCVCNA.TYCDSFDPPT.FPALGTPSRY.ESTRSGRRME.
1         11         21         31         41
LSMGPIQANH.TGTGLLLTLQ.PEQKFQKVKG.FGGAMTDAAA.LNILALSPPA.
51        61         71         81         91
QNLLLKSYFS.EEGIGYNIIR.VPMASCDFSI.RTYTYADTPD.DFQLHNFSLP.
101       111        121        131        141
EEDTKLKIPL.IHRALQLAQR.PVSLLASPWT.SPTWLKTNGA.VNGKGSLKGQ.
151       161        171        181        191
PGDIYHQTWA.RYFVKFLDAY.AEHKLQFWAV.TAENEPSAGL.LSGYPFQCLG.
201       211        221        231        241
FTPEHQRDFI.ARDLGPTLAN.ST*-225HHNVRLLM.LDDQRLLLPH.
251       261        271            281
WAKVVLTDPE.AAKYVHGIAV.HNYLDFLAPA.KATLGETHRL.FPNTMLFASE.
291       301        311        321        331        340
*-150ACVGSKF[WEQ.SVRLGSWDRG.MQYSHSIITN.LLYHVVGWID.
       341        351        361        371
WNLALNDEGG.PHRVRNFVDS.PIIVDETKDT.FYKQPMFYHL.GH]*-75
381       391        399401      411        421
PSKFIPEG.SQRVGLVASQ.KNDLDAVALM.HPDGSAVVVV.LNRSSKDVPL.
          431        441        451        461
TIKD*-23 PAVGFL.ETISPGYSIH.TYLWRRQ
471       481        491   497
```

FIG 6A Wt GCase (TKD)
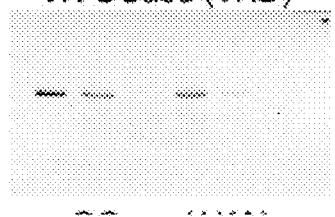
FIG 6B GCase (AAA)
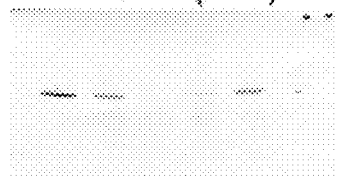
FIG 6C GCase (AKA)
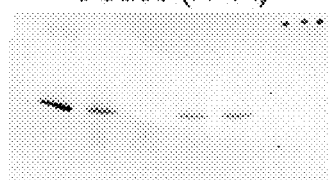
1 2 3 4 5 6
FIG 6D GCase (TAD)
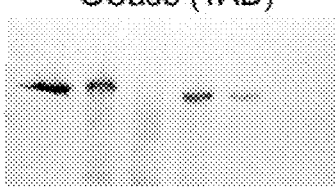
1 2 3 4 5 6
FIG 6E 1 2 3 4 5 6
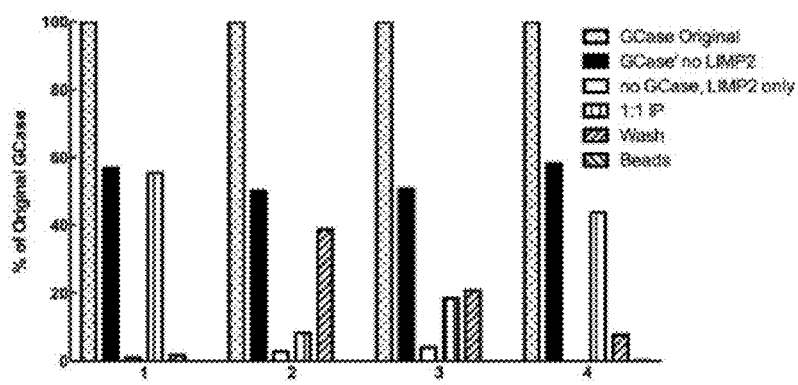

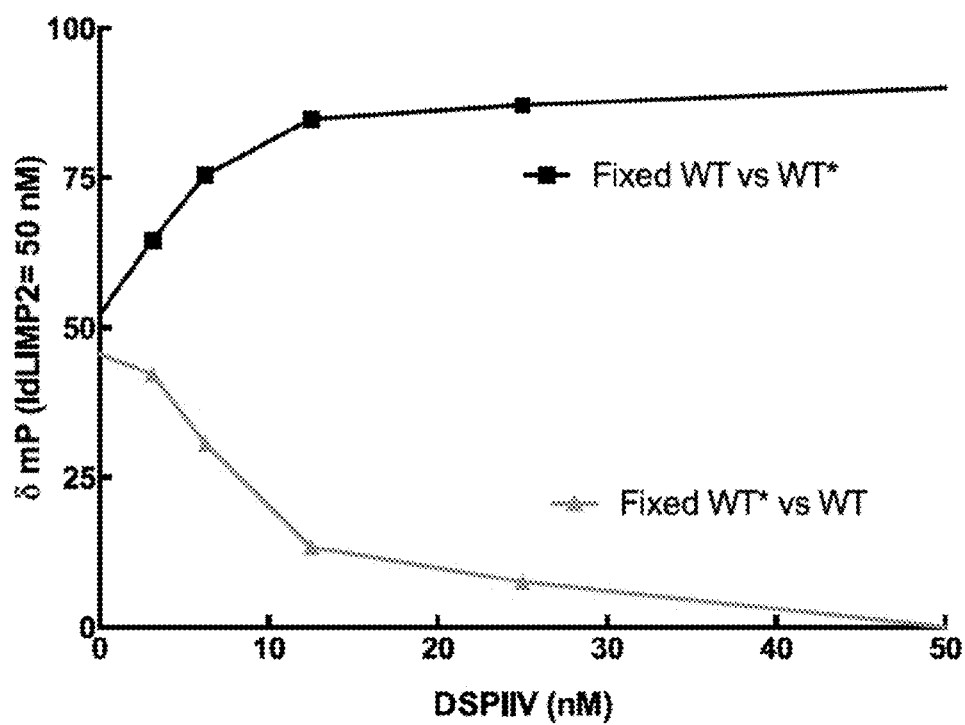

SEQUENCE LISTING

<160> NUMBER OF SEQ ID NOS: 24

<210> SEQ ID NO 1
<211> LENGTH: 2582
<212> TYPE: DNA
<213> ORGANISM: Homo sapiens

<400> SEQUENCE: 1

| | | | | | |
|---|---|---|---|---|---|
| ctctctctct | ctcgctcgct | ctctcgctct | ctcgctctct | ctcgctcgct | ctctcgctct | 60 |
| cgctctctct | ctctctccgg | ctcgccagcg | acacttgccg | ttcaacttga | ccaatgagac | 120 |
| ttgaggaagg | gctctgagtc | ccgcctctgc | atgagtgacc | gtctcttttc | caatccaggt | 180 |
| cccgccccga | ctcccagggg | ctgctttttct | cgcggctgcg | ggtggtcggg | ctgcatcctg | 240 |
| ccttcagagt | cttactgcgc | ggggcccccag | tctccagtcc | cgcccaggcg | cctttgcagg | 300 |
| ctgcggtggg | atttcgtttt | gcctccggtt | ggggctgctg | tttctcttcg | ccgacgtgga | 360 |
| tcctctatcc | ttcagagact | ctggaacccc | tgtggtcttc | tcttcatcta | atgaccctga | 420 |
| ggggatggag | ttttcaagtc | cttccagaga | ggaatgtccc | aagcctttga | gtagggtaag | 480 |
| catcatggct | ggcagcctca | caggattgct | tctacttcag | gcagtgtcgt | gggcatcagg | 540 |
| tgcccgcccc | tgcatcccta | aaagcttcgg | ctacagctcg | gtggtgtgtg | tctgcaatgc | 600 |
| cacatactgt | gactccttg | accccccgac | ctttcctgcc | cttggtacct | tcagccgcta | 660 |
| tgagagtaca | cgcagtgggc | gacggatgga | gctgagtatg | gggcccatcc | aggctaatca | 720 |
| cacgggcaca | ggcctgctac | tgaccctgca | gccagaacag | aagttccaga | agtgaagggg | 780 |
| atttggaggg | gccatgacag | atgctgctgc | tctcaacatc | cttgccctgt | cacccctgc | 840 |
| ccaaaatttg | ctacttaaat | cgtacttctc | tgaagaagga | atcggatata | acatcatccg | 900 |
| ggtacccatg | gccagctgtg | acttctccat | ccgcacctac | acctatgcag | acacccctga | 960 |
| tgatttccag | ttgcacaact | tcagcctccc | agaggaagat | accaagctca | agatacccct | 1020 |
| gattcaccga | gccctgcagt | ggcccagcg | tcccgtttca | ctccttgcca | gcccctggac | 1080 |
| atcacccact | tggctcaaga | ccaatggagc | ggtgaatggg | aagggtcac | tcaagggaca | 1140 |
| gcccggagac | atctaccacc | agacctgggc | cagatacttt | gtgaagttcc | tggatgccta | 1200 |
| tgctgagcac | aagttacagt | tctgggcagt | gacagctgaa | aatgagcctt | ctgctgggct | 1260 |
| gttgagtgga | taccccttcc | agtgcctggg | cttcacccct | gaacatcagc | gagacttcat | 1320 |
| tgcccgtgac | ctaggtccta | ccctcgccaa | cagtactcac | cacaatgtcc | gcctactcat | 1380 |
| gctggatgac | caacgcttgc | tgctgcccca | ctgggcaaag | gtggtactga | cagacccaga | 1440 |
| agcagctaaa | tatgttcatg | gcattgctgt | acattggtac | ctggacttc | tggctccagc | 1500 |
| caaagccacc | ctagggggaga | cacaccgcct | gttccccaac | accatgctct | tgcctcaga | 1560 |
| ggcctgtgtg | ggctccaagt | tctgggagca | gagtgtgcgg | ctaggctcct | gggatcgagg | 1620 |
| gatgcagtac | agccacagca | tcatcacgaa | cctcctgtac | catgtggtcg | gctggaccga | 1680 |
| ctggaacctt | gccctgaacc | ccgaaggagg | acccaattgg | gtgcgtaact | tgtcgacag | 1740 |
| tcccatcatt | gtagacatca | ccaaggacac | gtttttacaaa | cagcccatgt | tctaccacct | 1800 |
| tggccacttc | agcaagttca | ttcctgaggg | ctcccagaga | gtggggctgg | ttgccagtca | 1860 |
| gaagaacgac | ctggacgcag | tggcactgat | gcatcccgat | ggctctgctg | ttgtggtcgt | 1920 |
| gctaaaccgc | tcctctaagg | atgtgcctct | taccatcaag | gatcctgctg | tgggcttcct | 1980 |
| ggagacaatc | tcacctggct | actccattca | cacctacctg | tggcgtcgcc | agtgatggaa | 2040 |
| cagatactca | aggaggcact | gggctcagcc | tgggcattaa | agggacagag | tcagctcaca | 2100 |

-continued

```
cgctgtctgt gactaaagag ggcacagcag ggccagtgtg agcttacagc gacgtaagcc    2160
caggggcaat ggtttgggtg actcactttc ccctctaggt ggtgccaggg gctggaggcc    2220
cctagaaaaa gatcagtaag ccccagtgtc cccccagccc ccatgcttat gtgaacatgc    2280
gctgtgtgct gcttgctttg gaaactgggc ctgggtccag gctagggtg agctcactgt     2340 ccgtacaaac acaagatcag ggctgagggt aaggaaaaga agagactagg aaagctgggc    2400
ccaaaactgg agactgtttg tctttcctgg agatgcagaa ctgggcccgt ggagcagcag    2460
tgtcagcatc agggcggaag ccttaaagca gcagcgggtg tgcccaggca cccagatgat    2520
tcctatggca ccagccagga aaatggcag ctcttaaagg agaaaatgtt tgagcccagt     2580
ca                                                                   2582
```

<210> SEQ ID NO 2
<211> LENGTH: 497
<212> TYPE: PRT
<213> ORGANISM: Homo sapiens

<400> SEQUENCE: 2

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
```

275                 280                 285
Pro His Trp Ala Lys Val Val Leu Thr Asp Pro Glu Ala Ala Lys Tyr
    290                 295                 300
Val His Gly Ile Ala Val His Trp Tyr Leu Asp Phe Leu Ala Pro Ala
305                 310                 315                 320
Lys Ala Thr Leu Gly Glu Thr His Arg Leu Phe Pro Asn Thr Met Leu
                325                 330                 335
Phe Ala Ser Glu Ala Cys Val Gly Ser Lys Phe Trp Glu Gln Ser Val
            340                 345                 350
Arg Leu Gly Ser Trp Asp Arg Gly Met Gln Tyr Ser His Ser Ile Ile
        355                 360                 365
Thr Asn Leu Leu Tyr His Val Val Gly Trp Thr Asp Trp Asn Leu Ala
    370                 375                 380
Leu Asn Pro Glu Gly Gly Pro Asn Trp Val Arg Asn Phe Val Asp Ser
385                 390                 395                 400
Pro Ile Ile Val Asp Ile Thr Lys Asp Thr Phe Tyr Lys Gln Pro Met
                405                 410                 415
Phe Tyr His Leu Gly His Phe Ser Lys Phe Ile Pro Glu Gly Ser Gln
            420                 425                 430
Arg Val Gly Leu Val Ala Ser Gln Lys Asn Asp Leu Asp Ala Val Ala
        435                 440                 445
Leu Met His Pro Asp Gly Ser Ala Val Val Val Leu Asn Arg Ser
    450                 455                 460
Ser Lys Asp Val Pro Leu Thr Ile Lys Asp Pro Ala Val Gly Phe Leu
465                 470                 475                 480
Glu Thr Ile Ser Pro Gly Tyr Ser Ile His Thr Tyr Leu Trp Arg Arg
                485                 490                 495
Gln

<210> SEQ ID NO 3
<211> LENGTH: 11
<212> TYPE: PRT
<213> ORGANISM: Artificial Sequence
<220> FEATURE:
<223> OTHER INFORMATION: GCase-LIMP2 binding sequence

<400> SEQUENCE: 3

Asp Ser Pro Ile Ile Val Asp Ile Thr Lys Asp
1               5                   10

<210> SEQ ID NO 4
<211> LENGTH: 176
<212> TYPE: PRT
<213> ORGANISM: Artificial Sequence
<220> FEATURE:
<223> OTHER INFORMATION: AA 247-422 of GCase

<400> SEQUENCE: 4

Phe Gln Cys Leu Gly Phe Thr Pro Glu His Gln Arg Asp Phe Ile Ala
1               5                   10                  15
Arg Asp Leu Gly Pro Thr Leu Ala Asn Ser Thr His His Asn Val Arg
            20                  25                  30
Leu Leu Met Leu Asp Asp Gln Arg Leu Leu Leu Pro His Trp Ala Lys
        35                  40                  45
Val Val Leu Thr Asp Pro Glu Ala Ala Lys Tyr Val His Gly Ile Ala
    50                  55                  60
Val His Trp Tyr Leu Asp Phe Leu Ala Pro Ala Lys Ala Thr Leu Gly

```
                65                  70                  75                  80
Glu Thr His Arg Leu Phe Pro Asn Thr Met Leu Phe Ala Ser Glu Ala
                    85                  90                  95
Cys Val Gly Ser Lys Phe Trp Glu Gln Ser Val Arg Leu Gly Ser Trp
                100                 105                 110
Asp Arg Gly Met Gln Tyr Ser His Ser Ile Ile Thr Asn Leu Leu Tyr
                115                 120                 125
His Val Val Gly Trp Thr Asp Trp Asn Leu Ala Leu Asn Pro Glu Gly
    130                 135                 140
Gly Pro Asn Trp Val Arg Asn Phe Val Asp Ser Pro Ile Ile Val Asp
145                 150                 155                 160
Ile Thr Lys Asp Thr Phe Tyr Lys Gln Pro Met Phe Tyr His Leu Gly
                165                 170                 175

<210> SEQ ID NO 5
<211> LENGTH: 13
<212> TYPE: PRT
<213> ORGANISM: Artificial Sequence
<220> FEATURE:
<223> OTHER INFORMATION: AA 397-409 of GCase

<400> SEQUENCE: 5

Phe Val Asp Ser Pro Ile Ile Val Asp Ile Thr Lys Asp
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Wildtype

<400> SEQUENCE: 6

Asp Ser Pro Ile Ile
1               5

<210> SEQ ID NO 7
<211> LENGTH: 5
<212> TYPE: PRT
<213> ORGANISM: Artificial Sequence
<220> FEATURE:
<223> OTHER INFORMATION: Peptide

<400> SEQUENCE: 7

Ala Ser Pro Ile Ile
1               5

<210> SEQ ID NO 8
<211> LENGTH: 5
<212> TYPE: PRT
<213> ORGANISM: Artificial Sequence
<220> FEATURE:
<223> OTHER INFORMATION: Peptide

<400> SEQUENCE: 8

Asp Ser Ala Ile Ile
1               5

<210> SEQ ID NO 9
<211> LENGTH: 5
<212> TYPE: PRT
<213> ORGANISM: Artificial Sequence
<220> FEATURE:
<223> OTHER INFORMATION: Peptide
```

<400> SEQUENCE: 9

Asp Ser Pro Ala Ile
1               5

<210> SEQ ID NO 10
<211> LENGTH: 5
<212> TYPE: PRT
<213> ORGANISM: Artificial Sequence
<220> FEATURE:
<223> OTHER INFORMATION: Peptide

<400> SEQUENCE: 10

Asp Ser Pro Ile Ala
1               5

<210> SEQ ID NO 11
<211> LENGTH: 5
<212> TYPE: PRT
<213> ORGANISM: Artificial Sequence
<220> FEATURE:
<223> OTHER INFORMATION: Peptide

<400> SEQUENCE: 11

Ala Ser Pro Ile Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Peptide

<400> SEQUENCE: 12

Ala Ser Pro Ala Ala
1               5

<210> SEQ ID NO 13
<211> LENGTH: 11
<212> TYPE: PRT
<213> ORGANISM: Artificial Sequence
<220> FEATURE:
<223> OTHER INFORMATION: GCase consensus sequence

<400> SEQUENCE: 13

Asp Ser Pro Ile Ile Val Asp Ile Ala Lys Asp
1               5                   10

<210> SEQ ID NO 14
<211> LENGTH: 7
<212> TYPE: PRT
<213> ORGANISM: Artificial Sequence
<220> FEATURE:
<223> OTHER INFORMATION: GCase di-leucine sequence

<400> SEQUENCE: 14

Asp Asp Gln Arg Leu Leu Leu
1               5

<210> SEQ ID NO 15
<211> LENGTH: 6
<212> TYPE: PRT
<213> ORGANISM: Artificial Sequence
<220> FEATURE:
<223> OTHER INFORMATION: GCase wild type peptide

```
<400> SEQUENCE: 15

Asp Ser Pro Ile Ile Val
1               5

<210> SEQ ID NO 16
<211> LENGTH: 6
<212> TYPE: PRT
<213> ORGANISM: Artificial Sequence
<220> FEATURE:
<223> OTHER INFORMATION: Peptide

<400> SEQUENCE: 16

Ala Ser Pro Ile Ile Val
1               5

<210> SEQ ID NO 17
<211> LENGTH: 6
<212> TYPE: PRT
<213> ORGANISM: Artificial Sequence
<220> FEATURE:
<223> OTHER INFORMATION: Peptide

<400> SEQUENCE: 17

Asp Ser Pro Ala Ile Val
1               5

<210> SEQ ID NO 18
<211> LENGTH: 6
<212> TYPE: PRT
<213> ORGANISM: Artificial Sequence
<220> FEATURE:
<223> OTHER INFORMATION: Peptide

<400> SEQUENCE: 18

Asp Ser Pro Ile Ala Val
1               5

<210> SEQ ID NO 19
<211> LENGTH: 6
<212> TYPE: PRT
<213> ORGANISM: Artificial Sequence
<220> FEATURE:
<223> OTHER INFORMATION: Peptide

<400> SEQUENCE: 19

Asp Ser Pro Ala Ala Val
1               5

<210> SEQ ID NO 20
<211> LENGTH: 6
<212> TYPE: PRT
<213> ORGANISM: Artificial Sequence
<220> FEATURE:
<223> OTHER INFORMATION: Peptide

<400> SEQUENCE: 20

Glu Ser Pro Ile Ile Val
1               5

<210> SEQ ID NO 21
<211> LENGTH: 5
<212> TYPE: PRT
<213> ORGANISM: Artificial Sequence
<220> FEATURE:
<223> OTHER INFORMATION: Peptide

<400> SEQUENCE: 21
```

```
Glu Ser Ala Ile Ile
1               5

<210> SEQ ID NO 22
<211> LENGTH: 5
<212> TYPE: PRT
<213> ORGANISM: Artificial Sequence
<220> FEATURE:
<223> OTHER INFORMATION: Peptide

<400> SEQUENCE: 22

Glu Ser Pro Ala Ile
1               5

<210> SEQ ID NO 23
<211> LENGTH: 5
<212> TYPE: PRT
<213> ORGANISM: Artificial Sequence
<220> FEATURE:
<223> OTHER INFORMATION: Peptide

<400> SEQUENCE: 23

Glu Ser Pro Ile Ala
1               5

<210> SEQ ID NO 24
<211> LENGTH: 39
<212> TYPE: PRT
<213> ORGANISM: Artificial Sequence
<220> FEATURE:
<223> OTHER INFORMATION: Peptide

<400> SEQUENCE: 24

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly
            35
```

LYSOSOMAL PROTEIN TARGETING SEQUENCE AND THERAPEUTIC APPLICATIONS OF SAME

CROSS REFERENCE TO RELATED APPLICATIONS

This application claims the benefit of and priority to U.S. Provisional Application 61/882,272, filed Sep. 25, 2013, which is incorporated in its entirety for all purposes.

STATEMENT REGARDING FEDERALLY SPONSORED RESEARCH OR DEVELOPMENT

This invention was made with government support under DK036729 awarded by the National Institutes of Health. The government has certain rights in the invention.

BACKGROUND

For integral lysosomal membrane proteins, specific peptide sequences are essential for their delivery to the lysosomes. These are the M6P-independent targeting systems that rely on peptide sequences and not M6P or other carbohydrate recognition systems. Inherent in the original concept of the lysosome, as described by deDuve (1), is an essential mechanism to localize or target specific proteins/enzymes to this subcellular organelle. Goldstein and Brown were awarded a Nobel Prize for their discovery and elucidation of specific receptors on cells for the uptake of extracellular low-density lipoproteins into the cell and delivery to the lysosomes (2, 3). Later this concept of receptor-mediated endocytosis was generalized to include not only extracellular ligand-receptor interactions, but also the essential need for such a system within cells for delivery/targeting of newly synthesized proteins to the lysosomes. One such system was elucidated by Kornfeld and coworkers (4) and Sly and coworkers (5, 6) and is now known as the mannose-6-phosphate (M6P) system. This M6P is used by many of the soluble proteins for their delivery to the lysosomes. The deficiency of the ability to attach M6P to such proteins results in the secretion of several dozen proteins from the cell and a progressive multisystem fatal disease termed MLII/MLIII (7).

M6P and mannose receptor systems form the essential basis for the delivery of administered recombinant proteins for the treatment of the so-called lysosomal storage diseases (8). Production of lysosomal proteins for delivery to specific affected tissues is completely dependent upon understanding what receptor is critical to those tissues for uptake, internalization, and delivery of the therapeutic proteins to the lysosomes (8). For example, the mannose-receptor is significantly represented on macrophages and other cells of the reticuloendothelial system (RES). Gaucher disease has its major disease manifestations in macrophages and the RES. Effective enzyme therapy was developed based on the ability to create recombinant acid β-glucosidase, the defective enzyme in Gaucher disease, with mannose terminated oligosaccharide residues (9, 10). For Fabry disease, Pompe disease and Mucopolysaccharidoses I, II, and VI, recombinant enzymes with M6P oligosaccharides have become the standards of care for the treatment of these diseases (e.g. 11, 12). The successes in treating these formerly fatal and severely debilitating diseases have been documented extensively. The total sales of enzymes for the treatment of these diseases now exceed $5 B annually.

There remain several membrane associated, not integral membrane, proteins that appear to have a completely different system for targeting to the lysosomes. One such protein is an enzyme, termed acid β-glucosidase, which is defective in Gaucher disease, the most common lysosomal storage disease (13). Acid β-glucosidase (also referred to as D-glucosyl-N-acylsphingosine glucohydrolase, glucocerebrosidase, GCase, assigned Enzyme Commission No. EC 3.2.1.45) is a lysosomal exoglycosidase for β-glucose-terminated sphingolipids (14,15). Insufficient activity of GCase is causal to the variants of Gaucher disease, a common lysosomal storage disease (16). The human or mouse genes, GBA1 or Gba1, respectively, are about 7.5 kb and contain 11 exons, which encodes a highly (~86% identical/92% similar) conserved amino acid sequence. Over 300 mutations of various types have been found in association with the variants of Gaucher disease and some have clear prognostic value for affected patients (17). Each of the resultant different single amino acid substitutions lead to GCases with altered catalytic, stability, or both defects (e.g., 18). GCase is translated from mRNAs into a protein that contains two functional, in tandem, leader sequences that differ in length, either 39 (SEQ ID NO 24) or 19 amino acids (19). The preferred initiation codon is not known.

Mature GCase is a glycoprotein of 497 amino acids (FIG. 3, SEQ ID NO 2) that is produced by co-translational glycosylation of four of five N-glycosylation sequences (N463 not occupied) of which only N-19 is essential for the formation of a catalytically active conformer (20). The enzyme also has properties of a membrane associated, but not transmembrane, protein. Unlike most soluble lysosomal proteins that are trafficked to the lysosome by the mannose-6-phosphate (M6P) receptor system (21,22), GCase contains little if any M6P (23). Newly synthesized unglycosylated GCase is not secreted out of cells nor is enzyme secreted from I-Cell fibroblasts, which are deficient in the enzyme needed for M6P (21). Thus, the targeting to the lysosome of newly synthesized, intracellular, GCase is not oligosaccharide dependent (24).

Like the M6P targeting systems, non-carbohydrate-mediated lysosomal targeting disruptions lead to multisystem fatal diseases (8, 9). Lysosomal Integral Membrane Protein 2 (LIMP-2) has been identified as a trafficking receptor for GCase (23, 25, 26). LIMP-2 is a 478 amino acid, 85 Kd glycoprotein protein that is also known as SCARB-2/CD36L2. This protein is present in the ER, Golgi, endosomal, lysosomal, and plasma membrane compartments of cells (26, 27). As the name indicates, LIMP-2 is an integral membrane protein with N- and COOH-terminal transmembrane domains, and a luminal domain (ldLIMP-2) that binds GCase (23) and potentially other proteins. LIMP-2 binds to GCase in the ER (pH-6.8) and the enzyme remains bound to LIMP-2 during its transport through the Golgi, trans-Golgi network, and endosomal compartments. LIMP-2 delivers GCase to the lysosomes after an acidic pH-modulated dissociation of the receptor and ligand in the late endosomal compartment with liberation of GCase. This dissociation is mediated by LIMP-2 histidine 171 (28). No other proteins have been identified to bind to LIMP-2 inside of cells.

LIMP-2/SCARB-2 is also a scavenger receptor on the plasma membrane that binds peptide sequences of viruses, in particular enteroviruses (e.g. EV71), for internalization, lysosomal delivery and degradation (29-32). The ligand amino acid sequence of EV71 for human LIMP-2 has been identified within VP1 (30), which has no homology to GCase sequences. The corresponding receptor sequence on LIMP-2 is between amino acids 144-151 (28). Other LIMP- 2/SCARB-2 protein ligands that bind at the plasma membrane include KCNQ1, KCNE2, and Megalin (33).

Humans and mice with mutations in the LIMP-2 gene develop characteristic neurologic and renal diseases, but do not exhibit gross findings of Gaucher disease, i.e., GC storage or Gaucher cells (33, 34). The human diseases associated with LIMP-2 mutations are termed the action myoclonus-renal failure syndrome (34). LIMP-2 deficient cells in humans and mice exhibit excess secretion of GCase out of the cells and into plasma or culture media, but little GC accumulation in tissues (34, 23). LIMP-2 variants have also been implicated as potential modifiers in the development of Parkinson/Alzheimer diseases (35, 36, 33), as have GBA1 mutations (36-39). Disruption of appropriate trafficking of GCase to the lysosome may provide a mechanistic basis for the impact of GBA1/Gba1 mutations in the modification of α-synuclein metabolism and its role in Parkinson disease (37, 38, 40). The impact of LIMP-2 on the expression of Gaucher disease and both GCase and LIMP-2 variants as modifiers of synucleinopathies highlight the importance of understanding the interactions of GCase and LIMP-2 and the localization of synthesized GCase to the lysosome.

Thus, there remains a need for methods and compositions effective for treating lysosomal storage diseases related to defects in the acid β-glucosidase pathway such as Gaucher disease. Further, there is a need for treatments of disease states related to dysregulation of synuclein metabolism that may result from, or be exacerbated by, disruption of appropriate trafficking of GCase to the lysosome, such as neurodegenerative disease states including Parkinson disease, Alzheimer disease, and Lewy body disease. Finally, there remains a need for improved methods of synthesizing recombinant GCase, which can subsequently be used to treat disease states resulting from deficiencies in this enzyme. The instant disclosure seeks to address one or more of these needs.

BRIEF SUMMARY

Disclosed herein are methods of treating disease states including lysosomal storage diseases and/or neurodegenerative diseases. Further disclosed are compositions useful for the disclosed methods.

BRIEF DESCRIPTION OF THE DRAWINGS

The drawings are for illustration purposes only, not for limitation.

FIG. 3: Mature WT GCase amino acid sequence highlighting the regions targeted for mutagenesis, expression, and binding analyses. The amino acid sequence of GCase is marked with the various GCase-XX or XXX in blue to indicate the deleted parts of the enzyme. Shown in green is a typical dileucine sequence for indirect targeting of membrane bound lysosomal proteins. Shown in red are the amino acids for targeted mutagenesis and binding studies to ldLIMP-2. FIG. 13 shows the high conservation of these sequences.

FIG. 6A-6E: Immunoprecipitation of the alanine substituted GCases in the TKD sequence with ldLIMP2. In panels shown in FIG. 6A to FIG. 6D, the lanes 1 through 6 correspond to the band densities indicated by the bars in E. The panels show that the WT sequence (FIG. 6A) had nearly complete binding with ldLIMP2, i.e., retention on the beads to which ldLIMP2 was bound (Lane 4) and no GCase in the wash (Lane 5). In comparison, the triple alanine mutant (FIG. 6B) shows essentially no binding to ldLIMP2, i.e., all the GCase is in the wash (Lane 5). The AKA GCase mutant (FIG. 6C) showed about equal amounts of GCase in Lanes 4 and 5 or about 50% binding to ldLIMP2. The AKD GCase mutant (FIG. 6D) had binding pattern that was similar to the WT sequence, but with more GCase in the wash (Lane 5), i.e., somewhat less binding. The quantitative results are shown in (FIG. 6E) in which 1, 2, 3, and 4 correspond to WT, AAA, AKA, and AKD, respectively.

FIG. 7A-FIG. 7C: Binding and competition of fluorescent labeled or unlabeled DSPIIV (SEQ ID NO 15) GCase peptides to ldLIMP2. The change ($\delta mP$) in fluorescence polarization is plotted on the ordinate and the increasing concentrations of the various peptides are on the abscissa. FIG. 7A depicts saturation kinetics under conditions in which the concentration of ldLIMP2 (50 nM) was fixed. With the WT (DSPIIV (SEQ ID NO 15)) peptide (duplicate experiments in ● and ▼), saturation kinetics with about half maximal binding to ldLIMP2 was observed at 50 nM. The DSPAIV (SEQ ID NO 17) and DSPIAV (SEQ ID NO 18) mutants did not show saturation up to 250 nM, indicating their poor interaction with ldLIMP2. The ASPAAP peptide showed background changes. The ASPIIV peptide (SEQ ID NO 16) showed δmP values slightly above background indicating little binding to ldLIMP2. FIG. 7B depicts a similar study using unlabeled peptides as competitors. To ensure that the label did not interfere/promote binding, similar studies were conducted using fluorescently labeled peptides as binders and their respective unlabeled peptides as competitors. Each of the unlabeled peptides "competed" with the labeled peptides in the expected ratios. FIG. 7C depicts a competition study in which labeled (WT*) and unlabeled (WT) peptides were used in complementary competition studies. Either the labeled or unlabeled WT peptides equally competed for binding to ldLIMP2 showing both were equally effective in binding and that the label did not change the properties of the peptide-ldLIMP2 interaction.

FIG. 8A depicts immunoprecipitation of GCase and LIMP-2. Purified WT GCase was preincubated with purified ldLIMP2 in a molar ratio of 1:1. Then, unlabeled DSPIIV (SEQ ID NO 15) was added in varying molar excesses (0 to 5×, top of figure) over GCase, incubated, and then immunoprecipitated with Protein G-coupled anti-LIMP-2 antibody beads. The beads were then eluted and the eluants were analyzed for GCase and ldLIMP2 on Western blots using the specified antibodies. The results show decreasing amounts of bound GCase with increasing peptide molar ratios, i.e., peptide DSPIIV (SEQ ID NO 15) competed bound GCase off of ldLIMP2. In the bottom panel, ldLIMP2 recovery was the same at all peptide ratios. FIG. 8B depicts immunoprecipitation of GCase and LIMP-2. Purified ldLIMP2 was preincubated with unlabeled WT peptide at various molar ratios. Then, purified WT GCase was added in a 1:1 molar ratio with ldLIMP2, incubated, and then immunoprecipitated and processed as in FIG. 8A. The results show that the peptide prevents the binding of ldLIMP2 and WT GCase. FIG. 8C depicts immunoprecipitation of GCase and LIMP-2. Purified WT GCase was preincubated with purified ldLIMP2 in a molar ratio of 1:1. Then peptide DDQRLLL, a potential candidate for the GCase ligand for ldLIMP2, was added in varying molar excesses over WT GCase, incubated, and then immunoprecipitated and processed as in FIG. 8A. The results show that peptide DDQRLLL (SEQ ID NO 14) did not compete GCase off of ldLIMP2, thereby showing that this peptide did not have specificity for the GCase binding site on ldLIMP2. DDQRLLL (SEQ ID NO 14) is a dileucine peptide outside of the localized targeting region of DSPI-IVDITKD (SEQ ID NO 3) (see FIG. 3).

FIG. 10A depicts typical examples of immunofluorescence localization of DSPIIV (SEQ ID NO 15) substituted GCase variants following transient transfections. The DSPIIV (SEQ ID NO 15) (WT) and ESPIIV (SEQ ID NO 20) show co-localization of GCase (FITC) with either Lamp1 (Red) or LIMP-2 (purple), indicating that the retention of charge by E399 does not impact localization. The cells are typical for either D399 (DSPIIV (SEQ ID NO 15)) or E399 (ESPIIV (SEQ ID NO 20)). The DSPAIV (SEQ ID NO 17) (I402A) or DSPIAV (SEQ ID NO 18) (I403A) mutant shows no co-localization with ldLIMP2 or Lamp1, i.e. no binding to ldLIMP2 in the cell and no localization to the lysosome (Lamp1/ldLIMP2). The black and white figures in the lower right indicate the relative localization of LAMP-1 (lysosomes) and WT GCase (ER/Golgi and Lysosomes) in Gba1−/− fibroblasts for comparison. FIG. 10B depicts Pearson Indices for co-localization of the various mutants in the ER/Golgi (black) or lysosome (hatched). The substitution of E for D (WT) at 399 (ESPIIV (SEQ ID NO 20)) did not alter the co-localization compared to WT. In comparison ASPIIV (SEQ ID NO 16) (D399A) and the double mutant, DSPAAV (SEQ ID NO 19) (I402A+I403A) showed little co-localization to the lysosome, but significant retention in the ER/Golgi. The single mutants, DSPAIV (SEQ ID NO 17) (I402A) and DSPIAV (SEQ ID NO 18) (I403A) showed partial co-localization to the lysosome, but greater retention in the ER/Golgi.

FIG. 11A depicts activities in the media of Gba1−/− fibroblasts following transient transfections of each of the specified alanine substituted GCases in the TDK region. Increases of 4 to 10-fold were found in the media with the mutant GCases, the AKD showed the greatest increases and the AAA the least. The right panel shows the CRIM Specific Activity, relative intrinsic catalytic activities of the TKD and its alanine substituted mutant variants. FIG. 11B depicts in the Left Panel: Activities in the media following transient transfections of various DSPIIV (SEQ ID NO 15) alanine substituted GCases and the % of GCase secreted. The latter was calculated as {ng GCase (in media)/[ng GCase (in media)+ng (GCase in lysates)]}×100 (also see Table 2). The ESPIIV (SEQ ID NO 20) GCase did not alter secretion, i.e., little enzyme in the media. All of the alanine substitutions in the DSPIIV (SEQ ID NO 15) sequence resulted in ~20-25 fold increase in GCase activity in the media (solid bars). The transfections alone (Null+lipo) had no effect. In comparison, the amount of secreted GCase protein varied between 22 and 83% (hatched bars) Right Panel: Shows the CRIM specific activity of WT and these same mutant GCases demonstrating that the mutations decreased this activity relative to WT as indicated above the bars. FIG. 11C depicts in cellular lysate GCase activities from the various alanine substituted GCases in the DSPIIV (SEQ ID NO 15) sequence as indicated. The WT and ESPIIV (SEQ ID NO 20) had equal intracellular activities of GCase, whereas the singly alanine substituted GCases had ~30% of WT levels. The doubly alanine substituted GCase had little intracellular activity, i.e., nearly all the GCase was secreted into the media.

FIG. 13A depicts the δmP of the WT (DDQRLLL (SEQ ID NO 14)) or variously alanine substituted labeled peptides plotted against the corresponding unlabeled peptide competitors. Note that the fixed ldLIMP2 concentration was 1000 nM or 20 times that used in similar studies (FIG. 7A-C). For all peptides the δmP were near or at background levels. FIG. 13B depicts the binding δmP for the various peptides as in FIG. 13A. The signals were near background levels for all peptides using concentrations 5 to 10 times that for DSPIIV (SEQ ID NO 15) and with a 20 times greater LIMP2 fixed concentration.

In FIG. 14A or FIG. 14B, ldLIMP2 and DDQRLLL (SEQ ID NO 14) were incubated before (as shown in FIG. 14A) or together with (as shown in FIG. 14B) GCase and analyzed as in FIG. 8A-C. Under either condition, the peptide did not complete with GCase for ldLIMP2 binding.

DETAILED DESCRIPTION

Figure 1:
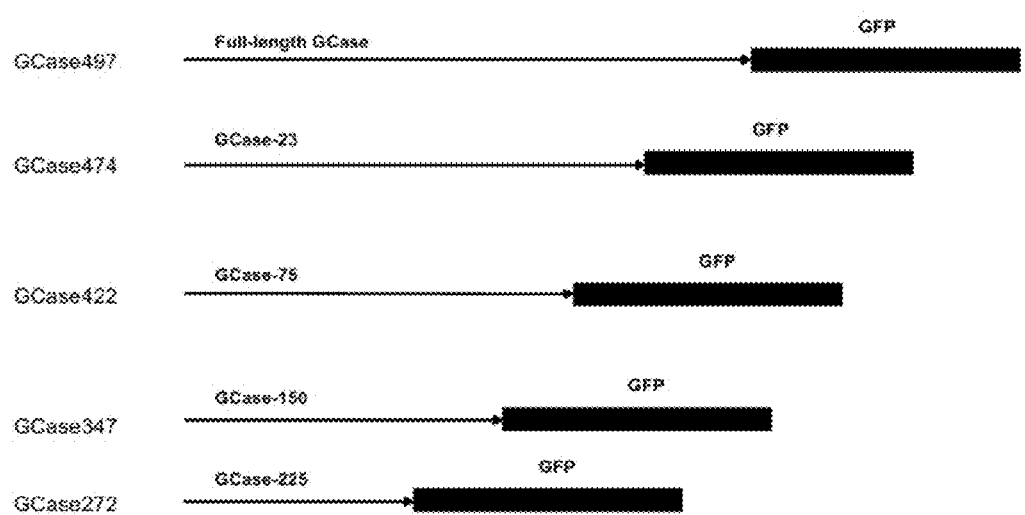
FIG. 1: GCase-GFP transfection constructs for Gba1 null/null cells. On the left are the resultant GCases following the various deletions and indicated as GCaseZZZ to show the encoded mature amino acid contents of the expressed enzymes. On the constructs are the labels GCase-XX or XXX to designate the number of amino acids that were deleted from the —COOH end of the mature 497 amino acid sequence of the WT GCase. GFP was cloned in frame with the WT or GCase-XX or XXX. These constructs were subsequently transfected into Gba1−/− fibroblasts.

As used in this application, the terms "about" and "approximately" are used as equivalents. Any numerals used in this application with or without about/approximately are meant to cover any normal fluctuations appreciated by one of ordinary skill in the relevant art.

Amelioration:

As used herein, the term "amelioration" is meant the prevention, reduction or palliation of a state, or improvement of the state of a subject. Amelioration includes, but does not require complete recovery or complete prevention of a disease condition. In some embodiments, amelioration includes reduction of accumulated materials inside cells of relevant diseases tissues.

Biologically Active:

As used herein, the phrase "biologically active" refers to a characteristic of any agent that has activity in a biological system, and particularly in an organism. For instance, an agent that when administered to an organism has a biological effect on that organism is considered to be biologically active. In particular embodiments, where a protein or peptide is biologically active, a portion of that protein or peptide that shares at least one biological activity of the protein or peptide is typically referred to as a "biologically active" portion. Biological activity can include, for example, enzyme activity and/or the trafficking activity necessary for biological function.

Improve, Increase, or Reduce:

As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of a disease as the individual being treated, who is about the same age as the individual being treated (to ensure that the stages of the disease in the treated individual and the control individual(s) are comparable).

Individual, Subject, Patient:

As used herein, the terms "subject," "individual" or "patient" refer to a human or a non-human mammalian subject. The individual (also referred to as "patient" or "subject") being treated is an individual (fetus, infant, child, adolescent, or adult human) suffering from one or more disease as disclosed herein.

Polypeptide, Peptide:

As used herein, a "polypeptide" or "peptide", generally speaking, is a string of at least two amino acids attached to one another by a peptide bond. In some embodiments, a peptide may include at least 3-5 amino acids, each of which is attached to others by way of at least one peptide bond. Those of ordinary skill in the art will appreciate that peptides sometimes include "non-natural" amino acids or other entities that nonetheless are capable of integrating into a polypeptide chain, optionally.

Substantial Homology:

The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial Identity:

The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in*

*Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Therapeutically Effective Amount:

As used herein, the term "therapeutically effective amount" refers to an amount of a therapeutic protein or peptide that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein, peptide, or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment:

As used herein, the term "treatment" (also "treat" or "treating") refers to any administration of a therapeutic protein (e.g., GCase or a peptide as described herein) that partially or completely alleviates, ameliorates, relieves, inhibits, delays onset of, reduces severity of and/or reduces incidence of one or more symptoms or features of a particular disease, disorder, and/or condition (e.g., a lysosomal storage disease such as Gaucher disease or a neurodegenerative disease). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

The peptide sequences on GCase and others like it that target the enzyme to the lysosome have not been elucidated prior to Applicant's disclosure herein. Here, Applicant has identified the peptide sequence on mature human GCase that is the ligand for LIMP-2 and has further identified novel mutations at specific amino acids that alter the localization within and secretion of GCase from cells.

In particular, disclosed is a new peptide sequence, not previously recognized, on GCase, that is essential for its targeting to the lysosome. Also disclosed are novel and innovative methods for the treatment of diseases, including lysosomal storage diseases such as Gaucher disease and its carrier state, as well as neurodegenerative diseases including Parkinsonism and Alzheimer disease. The connections between Gaucher disease and these much more common diseases was recently made by several groups, including Applicant's (39-42).

Applicant has identified the GCase binding sequence to the luminal domain of LIMP-2 ("ldLIMP-2") using heterologous expression of deletion constructs, the available GCase crystal structures, and by binding and colocalization of identified peptides or mutant GCases. These studies show a complex interaction of ldLIMP-2 with the highly conserved 11 amino acid sequence, DSPIIVDITKD (SEQ ID NO: 3), within human GCase. The binding is not dependent upon a single amino acid, but its interactions with LIMP-2 are heavily influenced by D399 (D399E having been identified as an equally effective residue, as described below) and the di-isoleucines, I402 and I403. Single alanine substitutions at any of these positions decreases binding to ldLIMP-2 and alters their pH dependent ldLIMP-2 binding as well as diminishing GCase's trafficking to the lysosome while increasing significantly GCase secretion. Thus, by mutation at any or all of these positions, or a combination thereof, decreased GCase binding and increased GCase secretion can be achieved. Replacement of the di-isoleucines and D399 with alanines obliterated binding to ldLIMP-2 and lysosomal localization.

However, the retention of the charge at D399, i.e., E399, did not alter the cellular localization or secretion of GCase. In comparison, alanine replacements in the TKD sequence (positions 407-409) showed less profound effects on ldLIMP-2 binding as single substitutions, i.e., TAD, compared to double, AKA, or triple, AAA, substituted GCases. Finally, the lack of trafficking to the lysosome of the deletion construct GCase-150 that contains the DDQRLLL (SEQ ID NO 14) sequence and the lack of binding of DDQRLLL (SEQ ID NO 14) peptides to ldLIMP-2, eliminates this known indirect lysosomal trafficking signal from participation in GCase targeting. This is a surprising result, in that DDQRLLL (SEQ ID NO 14) includes a known motif for lysosomal targeting of transmembrane lysosomal proteins and is highly conserved throughout phylogeny.

The GCase 11 amino acid ligand for LIMP-2 identified by Applicant is highly conserved throughout phylogeny with near identity at 10 of the amino acids. T407 of the human GCase has an alanine substitution in several mammalian lysosomal GCases so that the consensus sequence across 60 species including some insects and worms is DSPIIVDI-AKD (SEQ ID NO 13). Also, only in mosquito does the E399 equivalent occur, though, as stated above, the D399E mutant has binding properties identical to that of the human WT sequence. The IIV motif is identical across most of the species and in the few with variation, the branch chain amino acid V is substituted for either of the I, usually the I402 equivalent.

Enterovirus 71 causes foot and mouth disease by gaining access to cells after binding to LIMP-2/SCARB2 (30-32). The binding sequence on Enterovirus 71 for LIMP-2/SCARB2 has been localized to between VP1 amino acids 152 and 178 (30), but BLAST searches with the entire virus revealed no significant similarity to GCase and specifically in the 11 amino acid region. Several other proteins, e.g., KCNQ1, KCNE2, and Megalin, interact with LIMP-2/SCARB2 at the plasma membrane (33), but these do not share any homology with GCase. Other intracellular proteins that bind to LIMP-2 have not been identified (33). Because the LIMP-2/SCARB2 binding sequences for Enterovirus 71 and GCase are not similar, LIMP-2/SCARB2 may have a structure that contains multiple binding sites with differing specificities. Such structures are present in other receptors for carbohydrates, i.e., the macrophage mannose receptor that contains multiple carbohydrate binding domains with differing affinities/specificities for mannosyloligosaccharides (43, 44). Also, the cationic independent mannose-6-phosphate receptor/insulin-like growth factor receptor 2 has differing specificities for mannose 6-phosphate containing glycoproteins and prorenin (8, 45). Indeed, the residues on LIMP-2/SCARB2, which are critical to GCase binding, are within the same large segment of the receptor (residues 142-204) that may interact with a "canyon" for the virus and potentially the sequence of GCase binding. LIMP-2/SCARB2 residue H171 in this region appears critical to GCase binding, whereas amino acids 144-151 are essential for Enterovirus 71 binding and infectivity (30). Consequently, the region of binding for these two disparate proteins with different ligand sequences occurs in a region with overlapping, but apparently distinct, critical residues.

Such specificities are important for understanding the biology of LIMP-2 as are the other intracellular proteins that may bind to LIMP-2/SCARB2. For example, mutations in LIMP-2 are causal to a human and mouse disease, termed action myoclonus-renal failure syndrome (AMRF) (34). To understand the biochemical bases of this disease, it will be critical to understand which proteins interact with LIMP-2/SCARB2 and cause AMRF rather than Gaucher disease-like manifestations. However, being a heterozygote for a pathogenic LIMP-2/SCARB2 mutation potentiates the phenotype in Gaucher disease homozygotes (46) Additionally, disruptive mutations of GBA1 in the sequence critical to LIMP-2/SCARB2 may have more profound effects on the Gaucher disease phenotype then might be anticipated by the in vitro levels of residual activity, as the mutant protein may never reach the lysosome. The biology of LIMP-2/SCARB2 also may facilitate the understanding of the clear relationships between Parkinson disease and Lewy Body dementia. Indeed, the role of GCase binding to LIMP-2/SCARB2 in the ER may be important to the proposed feed forward mechanism of GCase/α-synuclein interaction (40) in the development and treatment of Parkinson disease and other α-synucleinopathies, such that interference of this binding may reverse or otherwise attenuate development of α-synucleinopathy disease states.

The precise role of LIMP-2 in trafficking GCase remains unexplored, but the studies here and in LIMP-2 deficient patients and mice offer some insights. GCase activity does not depend on whether it binds to LIMP-2. The poor or deficient binding of GCase variants to LIMP-2 in these studies does not appear to alter the enzyme activity or stability of GCase. Also, the LIMP-2 knock-out mouse cells produce active GCase, albeit at lower intracellular levels that WT (23), because of secretion from the cells. These findings suggest that, like the M6PR, LIMP-2 does not have a chaperone/protective function. LIMP-2/GCase binding also is not needed for GCase stability vis-à-vis saposin C's stabilization of GCase against proteolysis (47). Thus, LIMP-2/SCARB2's function is to deliver intracellularly synthesized GCases to the lysosomes.

The identification of a critical sequence for GCase binding to its receptor, LIMP-2/SCARB2 may have significant therapeutic implications. These studies indicate that GCases with specific mutations that disrupt binding to its receptor, but not its activity, could provide for enhanced secretion of GCase from cells for bulk production in selected cells. Since such mutations could greatly enhance the secretion of active enzyme suggesting the potential for enhanced production from mammalian or other systems that contain LIMP-2/SCARB2 analogues/homologues. Similarly, transplantation of specific cell types containing specifically expressing mutated GCases that interact poorly with LIMP-2, could supply large amount of secreted enzyme for therapeutic effects both in local and distant parts of the body. For example, for an enzyme that is normally not secreted, such secretion, attained by cellular replacement and/or gene therapy approaches with controllable expression elements, could provide a reservoir for the supply of secreted, active enzyme for cross correction in other cells. Such an approach would be particularly helpful in the CNS variants of Gaucher or Parkinson diseases, which are caused by or potentiated by GCase defects (48, 39) or the consequences of α-synucleinopathies (38, 49-51), and generalized distribution of the enzyme throughout the brain is currently not possible.

Modified GCase Protein (Recombinant Protein)

In one aspect, GCase proteins comprising one or more mutations are disclosed. By mutating the amino acid sequence in the wild-type GCase protein (SEQ ID NO:2), production of the recombinant protein may be significantly increased. This enzyme is not normally secreted from cells and, therefore, wild type enzyme produced is retained and is not available in the surrounding media for purification. Mutation of the GCase with retention of full activity can be accomplished and many fold greater levels of the enzyme can be recovered from the media as a potential therapeutic by site-specific mutation of the WT GCase protein as described herein. This has major advantages over existing approaches for the production of such proteins, allowing for improved methods of producing GCase which can subsequently be used to treat or reduce the effects of a variety of disease states as described herein.

In one aspect, disclosed herein are GCase proteins comprising one or more mutations that may comprise from about 85%, or from about 90%, or from about 95%, or from about 96%, or from about 97%, or from about 98%, or from about 99% sequence homology to human GCase sequence (SEQ ID NO 2), wherein the recombinant protein may comprise a mutation at one or more positions as described herein. In one aspect, the position wherein a mutation may occur is selected from position 397, 399, 400, 401, 402, 403, 408, 409, 410, and a combination thereof, with reference to SEQ ID NO 2. The one or more mutations decrease LIMP-2 binding, or in other aspects, substantially ablates LIMP-2 binding. In some aspects, the mutation may decrease binding by about 10%, or about 20%, or about 30%, or about 40%, or about 50%, or about 60%, or about 70%, or about 80%, or about 90% or about 100% as compared to WT binding. In one aspect, the mutation is such that the change in the amino acid changes the charge at the one or more mutated positions. In one aspect, the change is to a positively charged amino acid. In one aspect, the mutation may change the amino acid at the mutated position to an amino acid selected from alanine and glycine. In one aspect, the mutation may change the amino acid at the mutated position to alanine. It should be noted that, with respect to position 399, aspartate (D) may be mutated to glutamate (E) without effect to the binding. One of ordinary skill in the art will readily appreciate that certain amino acid substitutions are likely to be conservative in nature, such that a mutation at any one particular residue that is anticipated to be a conservative mutation is likely to have minimal effect on structure or function. As such, apart from and in addition to the described mutations above, Applicant notes that substantially homologous GCase proteins as defined above are within the scope of the disclosure.

In one aspect, the GCase protein may comprise a mutation at a position selected from 399, 402, 403, 407, 408, 409, and a combination thereof with reference to SEQ ID NO 2. In another aspect, the mutation may occur at a position selected from 399, 402, 403, and a combination thereof with reference to SEQ ID NO 2. In one aspect, positions 399-403 may be mutated such that this region of the sequence comprises a sequence selected from ASPII (SEQ ID NO 7), DSAII (SEQ ID NO 8), DSPAI (SEQ ID NO 9), DSPIA (SEQ ID NO 10), ASPIA (SEQ ID NO 11), ASPAA (SEQ ID NO 12). Similarly, the mutation may include any of the above sequences and further include the mutation D399E.

In one aspect, the mutation in the GCase protein may occur at a position selected from 407, 408, 409, and a combination thereof, with reference to SEQ ID NO 2. In one aspect, the amino acid sequence at positions 407-409 of SEQ ID NO 2 may comprise a sequence selected from AAA, AKA, and TAD. Again, it is to be recognized that D at position 409 may be mutated to E (glutamate) at position 409.

In one aspect, the GCase protein may comprise a mutation that decreases localization of the recombinant protein to the lysosomes of a cell while it is synthesized. In one aspect, the GCase protein comprising one or more mutations as described above may have biological activity and/or enzymatic activity that is substantially equivalent to that of wild type GCase. In one aspect, the GCase protein comprising one or more mutations may be capable of being taken up into cells via non-LIMP-2 mechanisms in substantially the same manner as wild type GCase. The GCase protein comprising one or more mutations may further comprise additional N-terminal and/or C-terminal amino acids. See, for example, variants disclosed in Brumshtein, B., et al. (2006). "Structural comparison of differently glycosylated forms of acid-beta-glucosidase, the defective enzyme in Gaucher disease." Acta Crystallogr D Biol Crystallogr 62 (Pt 12): 1458-1465, including a carrot cell variant, and a CHO cell expressed GCase comprising an amino acid arginine to histidine mutation at residue 495 (R495H). In one aspect, the GCase protein comprising one or more mutations as described herein may increase secretion of the recombinant protein or peptide from cells in which it is synthesized. It should be noted that the R495H mutant noted above is not believed to increase secretion as a result of the R to H mutation, but rather, secretion is likely due to heavy overexpression of the protein and saturation of LIMP-2.

In one aspect, the GCase protein comprising one or more mutations may provide significant advances for treatment. For example, the transformed and transplanted hematopoietic stem cells or transduced hepatic cells may be enabled to secrete large amounts of GCase that would function as an enzyme therapy in addition to the RES replacement via the hematopoietic system. These cells could be altered by, for example, in situ "gene therapy" by delivery of the gene therapeutic to the mature cells from the recipient or by use of induced pluripotent stem cell (iPSC)-derived progenitors that are genetically altered and returned to the same person from which the cells were derived, i.e., the donor and recipient are the same person.

In one aspect, the GCase proteins comprising one or more mutations described herein may be modified for use in neurological diseases in which gene therapy with GCase would be beneficial, i.e., Parkinson or Alzheimer diseases. For example, a gene therapy vector, e.g., AAV9/10 serotypes, for delivery of the cDNA for GCase to the striatal and/or hippocampal areas and the altered enzyme would be secreted in large amounts and result in metabolic correction of neighboring cells. In this case and in the case of using mutated GCase in hematopoietic stem cells or hepatic cells as described above, the enzyme may be taken up by other receptors because the peptide sequence does not participate in receptor-mediated endocytosis. Similarly, iPSC-derived neuronal progenitor cells (NPCs) could be genetically altered with the therapeutic hepatic cells and/or hematopoietic stem cells as described above, and then be used for intraventricular and/or stereotactic intracerebral injections. The former would require migration of the NPCs to areas of damage and the latter would require direct injection of the NPCs into areas of involvement. These approaches would lead to both cellular and enzyme reconstitution in the damaged brain.

Peptides

In one aspect, peptides are disclosed, wherein the peptide can be used as a therapeutic independently, or to facilitate any of the above-described methods without having to mutate the wild-type GCase. For example, the disclosed peptide would compete for the known receptor for this enzyme, LIMP2, and not allow the enzyme to be targeted to the lysosome, but rather to be shunted to the secretory pathway in large amounts.

In one aspect, peptides comprising residues 347 through 422 of SEQ ID NO 2 are disclosed. The peptides may be further combined with a pharmaceutically acceptable excipient for administration to a subject. In one aspect, the peptide binds to a LIMP-2 receptor. It should be noted that this is different than the enterovirus sequence that binds to LIMP-2. In one aspect, the peptide may comprise amino acids 397 through 409 of SEQ ID NO 2, or amino acids 399 through 403 of SEQ ID NO 2, or amino acids 407 through 409 of SEQ ID NO 2. Again, it is to be recognized that position 399 may be mutated to D399E. Likewise, aspartate (D) residues in the peptide sequences may generally be mutated to glutamate (E) residues while still preserving the binding of the peptide to a LIMP-2 receptor. The peptides described herein may prevent localization of GCase to a lysosome of a cell in which GCase is being synthesized and/or may increase secretion of endogenous GCase.

In some aspects, the peptides may comprise from about 3 to about 400, or about 3 to about 300, or about 3 to about 200, or about 3 to about 100, or about 3 to about 50, or about 3 to about 25, or about 3 to about 10 amino acid residues. In one aspect, the peptide may be a synthetic peptide of any length capable of being produced using methods known in the art. It will be appreciated that varying lengths of peptide sequences will be suited for administration as described herein, and that modification and manufacture of such peptides is well within the ordinary skill in the art.

DNA Vectors

In one aspect, DNA vectors capable of expressing a recombinant protein and/or peptide as described above are disclosed. Suitable vectors may include viral vectors, (including lenti, retro, AAV, Adeno, Herpes, rabies, any viral vector), plasmid vectors, cosmid vectors, or any other construct capable of expressing GCase proteins in cells containing LIMP-2 as will be readily understood by one of skill in the art.

Cell Lines

In one aspect, a cell or cell line that may comprise a DNA sequence capable of expressing a GCase protein comprising one or more mutations and/or a peptide as described above is disclosed. Cells suitable for use with the present disclosure will be readily apparent to one of ordinary skill in the art. For example, the cell may be selected from fibroblasts, or any other cell capable of producing the above-described proteins or peptides, including, for example, any nucleated cell, more particularly, CHO cells, human fibrosarcoma cells, carrot cells, a vertebrate cell that expressed LIMP-2, a hematopoietic stem cell, a transduced hepatic cell, a neuron, a microglial cell, or an induced pluripotent stem cell (iPSC)-derived progenitor. The cells may be transiently or stably transfected/transformed.

Methods of Treating Disease

In one aspect, one or more of the above-described GCase proteins or peptides may be used to treat one or more disorders or disease states in a subject in need thereof.

In one aspect, a method of inhibiting lysosomal LIMP2 is disclosed, wherein the method may comprise the step of administering one or more therapeutic agents selected from a GCase protein comprising one or more mutations as disclosed herein; a peptide as disclosed herein; a DNA vector as disclosed herein; a cell that produces a GCase protein comprising one or more mutations and/or a peptide as disclosed herein; or a combination thereof, to a patient in need thereof.

In one aspect, a method of treating a disorder related to a dysfunction in the GCase pathway is disclosed, the method comprising the step of administering one or more therapeutic agents selected from a GCase protein comprising one or more mutations as disclosed herein; a peptide as disclosed herein; a DNA vector as disclosed herein; a cell that produces a GCase protein comprising one or more mutations and/or a peptide as disclosed herein; or a combination thereof, to a patient in need thereof.

The disorders contemplated in the methods disclosed may comprise a disorder related to defective GCase activity and/or decreased enzymatic activity. In other aspects, the disorder may comprise a disorder associated with alpha-synuclein dysregulation. The disorder may comprise a lysosomal storage disease, for example, Gaucher disease, Fabry disease, Pompe disease, mucopolysaccharidoses, and multiple system atrophy. In other aspects, the disorder may comprise a neurodegenerative disorder, for example, Parkinson disease, Alzheimer disease, or Lewy body dementia. In one aspect, the disorder may comprise a dysfunction in the GCase pathway that results in a central nervous system disease wherein the pathogenesis of said disease results in plaques and/or disease states associated with plaques.

The methods may employ a variety of different routes of administration. In one aspect, the administration step may be selected from administration via intraventricular intracerebral injection, stereotactic intracerebral injection, intravenously, orally, subcutaneously, rectally, intranasally, via inhalation, and combinations thereof. In one aspect, for example, the method may comprise the step of administering one or more therapeutic agents as described herein via intraventricular and/or stereotactic intracerebral injection.

In a further aspect, the administration step may comprise isolation of a cell from a patient in need of treatment; introducing into the cell of the patient a sequence selected from a sequence capable of expressing a GCase protein comprising one or more mutations as disclosed herein, and/or a sequence capable of expressing a peptide as disclosed herein; and reintroducing the cell into the patient. In this aspect, the cell may then produce the GCase protein comprising one or more mutations and/or a peptide as disclosed herein.

EXAMPLES

Materials

The following were from commercial sources: 4-methylumbelliferyl-β-D-glucopyranoside (4MU-Glc; Biosynth AG, Switzerland); Sodium taurocholate (Calbiochem, La Jolla, Calif.); Rabbit anti-LIMP2 polyclonal antibody, rabbit anti-LAMP1 antibody, Goat anti-actin antibody (Santa Cruz BioT., Dallas, Tx); goat or rabbit anti-Calreticulin, -calnexin antibodies (Abcam, Cambridge, UK); NuPAGE 4-12% Bis-Tris gel, NuPAGE MES SDS running buffer, DMEM, pBluescript vector, Dynabeads protein G Immunoprecipitation Kits, BS3 chemical crosslinker (Invitrogen, Carlsbad, Calif.); BCA Protein Assay Reagent (Pierce, Rockford, Ill.); pCMV-AC-GFP/YFP/cMyc expression vectors (Origene, Rockville, Md.). PVDF membranes and ECL detection reagent (Amersham Biosciences, Piscataway, N.J.); ABC Vectastain and Alkaline Phosphatase Kit II (Black) (Vector Laboratory, Burlingame, Calif.). Restriction enzymes (New England Biolabs Inc., MD); site-directed mutagenesis kits (Clontech Lab. Inc., Mountain View, Calif. or QuikChange, Stratagene, TX). Purified luminal domain LIMP-2 (ld-LIMP2) was custom made (Sino Biological Inc., PRC.) Imiglucerase™ was a gift from Genzyme Corp. a Sanofi Company, Cambridge, Mass. Rabbit anti-GCase polyclonal antibody was produced in this laboratory (Fabbro D, and Grabowski G A. Human acid beta-glucosidase. Use of inhibitory and activating monoclonal antibodies to investigate the enzyme's catalytic mechanism and saposin A and C binding sites. J Biol Chem. 1991; 266(23):15021-7).

Methods:

Deletion constructs of GCases: The full-length human GCase cDNA in pBluescript was used as backbone for deletion constructs. Four single cut Restriction enzymes (ScaI, BstAPI, BalI and BamHI) were used to digest the full-length (FL) cDNA to created these deletion constructs (GCase-225, GCase-150, GCase-75 and GCase-23). These were subsequently individual clones into pCMV6-AC-GFP vector for mammalian cell expression to provide GCase-XX in frame with GFP. All constructs were resequenced for verification.

GCase expression constructs for point mutations: Using site-directed mutagenesis kits and designed primers, all single amino acid mutation constructs were created using the full Length pCMV-GCase-GFP or YFP vectors. All constructs were sequenced for verification and no or additional mutations were found.

Immunoprecipitation of GCases with mutations in the TKD sequence: For immunoblots, Gba1 knockout mouse fibroblasts (null/null) were transfected with the GBA1 constructs (WT or mutants) and expressed for 5 days. The GCases from harvested cell lysates were purified using a GCase antibody affinity column (Dynabeads protein G crosslinked (BS3) with rabbit anti-human GCase antibody). The purified GCases were then mixed with LIMP2 (1:1), incubated (30 min.), and applied to another affinity column (Dynabeads protein G crosslinked (BS3) with rabbit anti-LIMP2 antibody). Aliquots of each step (loading, wash and eluent) were collected and analyzed on 12.5% SDS gels. Immunoblots were developed using anti-human GCase antibody and AP conjugated color development kits. Mock experiments with either non-LIMP2 proteins added or no GCases added, were used as control. The quantitations of these immunoprecipitation data were obtained from densitometry measurements of the gels. The no-LIMP-2 bars are the controls for comparison, since GCase was processed through all steps without LIMP-2 to account for any losses of GCase; About 50% of the GCase was lost during processing.

Fluorescence Polarization: The DSPIIV (SEQ ID NO 15) and its mutants, and DDQRLLL (SEQ ID NO 14) peptides (FITC labeled or non-labeled) were synthesized (American Peptide Co., Vista, Calif.). Lyophilized peptides were solubilized in acetonitrile and then were diluted at least 10,000-fold into the reactions for fluorescence polarization assessments. The reactions were done at least in duplicate at various peptide and LIMP-2 concentrations (SpectraMax M5, Molecular Device). Fluorescence polarization data were collected and analyzed with SoftMax Pro 5.0 software. Reaction mixtures contained 100 mM phosphate, pH 6.8 and 1 mM DTT.

Immunofluorescence studies (IF): Mouse Gba1 null/null were used for the host cells for all transfection experiments. pCMV-AC-GFP Mammalian cell expression vector was used for expression of various GCases that included the TKD region (amino acids 407, 408 and 409) or the DSPIIV (SEQ ID NO 15) region (amino acids 399-404). Direct-labeled first antibodies were applied for IF detection; including anti-human GCase, -Calreticulin, -calnexin, -LIMP2, and -Lamp1. Lysotracker and ER tracker (Invitrogen) were also used as indicated. Analyses were done with a Zeiss AxioVert 200M with ApoTome. Co-localization analyses to obtain Pearson Indices were conducted using a module in the Axiovision 4.8 software.

Protein sequence homologies were performed using MUSCLE and BLAST (52, 53)

Enzyme Assays: Cell pellets were homogenized in 0.25% Na-taurocholate and 0.25% Triton X-100. GCase activities were determined fluorometrically with 4 mM 4MU-Glc in 0.2M/0.1M citric-phosphate, pH 5.6 (18, 54)

Results

Figure 2:
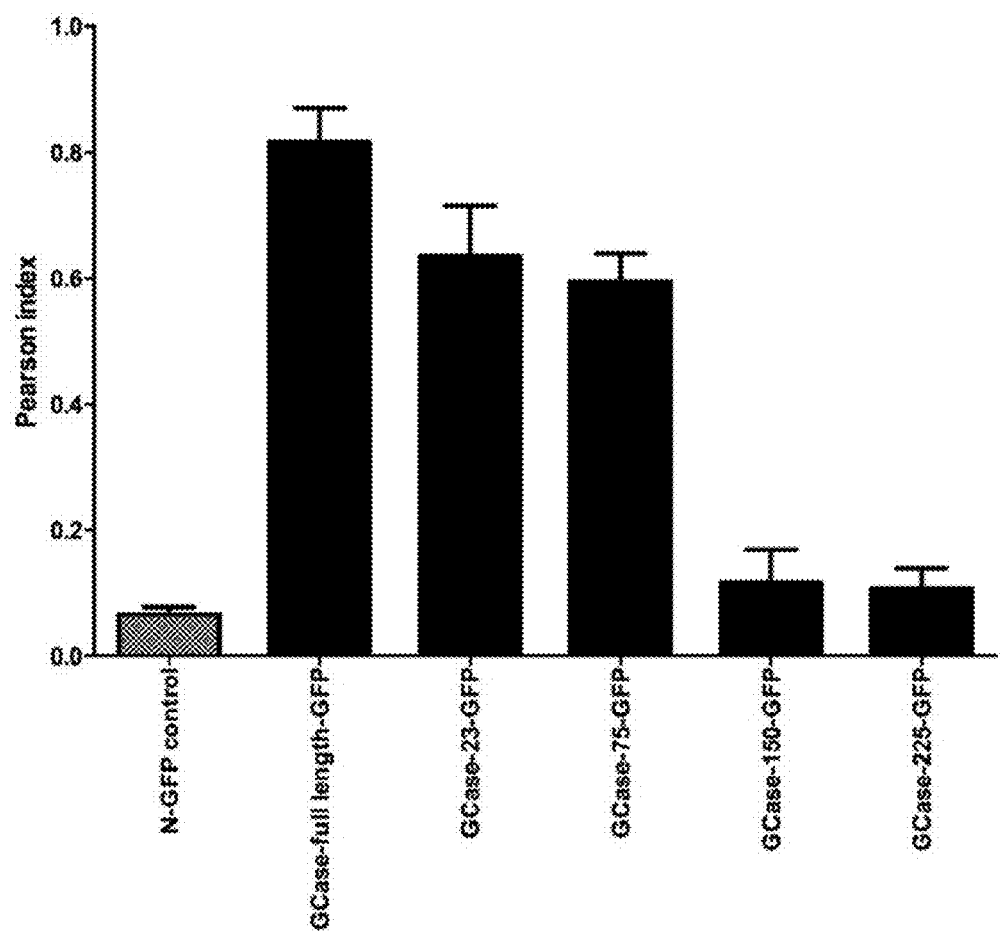
FIG. 2: Co-localization of GCase-XX- or -XXX-GFP with lysotracker. Pearson Indices were obtained (see Methods) for co-localization of the WT or truncated GCases using lysotracker to label the lysosomes. The construct containing only GFP (N-GFP) showed no co-localization. Compared to the WT sequence, GCase-23 and -75 showed only small decreases in lysosomal localization. GCase-150 and -225aa showed decreases in co-localization with lysotracker to nearly background (N-GFP) levels. GCase-150aa and -225aa showed much more extensive retention in the ER and Golgi compared to WT, GCase-23aa or GCase-75aa (data not shown).

Initial studies to localize the targeting peptide were conducted with GCase-GFP fusion constructs that had COOH-terminal deletions of GCase (FIG. 1). The constructs are designated as GCase-XX or XXX where the Xs represent the number of GCase amino acids deleted from the COOH-terminus. These constructs were transfected into and expressed in Gba1 null/null mouse fibroblasts using the CMV promoter (pCMV-AC-GFP or YFP) Immunofluorescence analyses using anti-human GCase IgG (green) and Lysotracker (Red) were used for colocalization of GCase to the lysosome (Red) or GCase (green) and Calreticulin or Calnexin (Red) for colocalization to the ER or Golgi (FIG. 2). The Pearson Indices for these immunofluorescence studies indicated that GCase-23 and GCase-75 had similar colocalization to the lysosome as full length WT GCase. In comparison, GCase-150 and GCase-225 were more localized to the ER and Golgi, and much less to the lysosome with Pearson Indices similar to the GFP control without GCase sequences (N-GFP). These studies showed that the critical GCase amino acids for targeting to the lysosome were between amino acids 347-422, i.e., in the fragment between GCase-75 and GCase-150. Since LIMP-2 is the receptor for targeting of GCase to the lysosome, our working hypothesis was that the peptide sequence for binding of GCase to LIMP-2 was located within amino acids 347-422.

Figure 4:
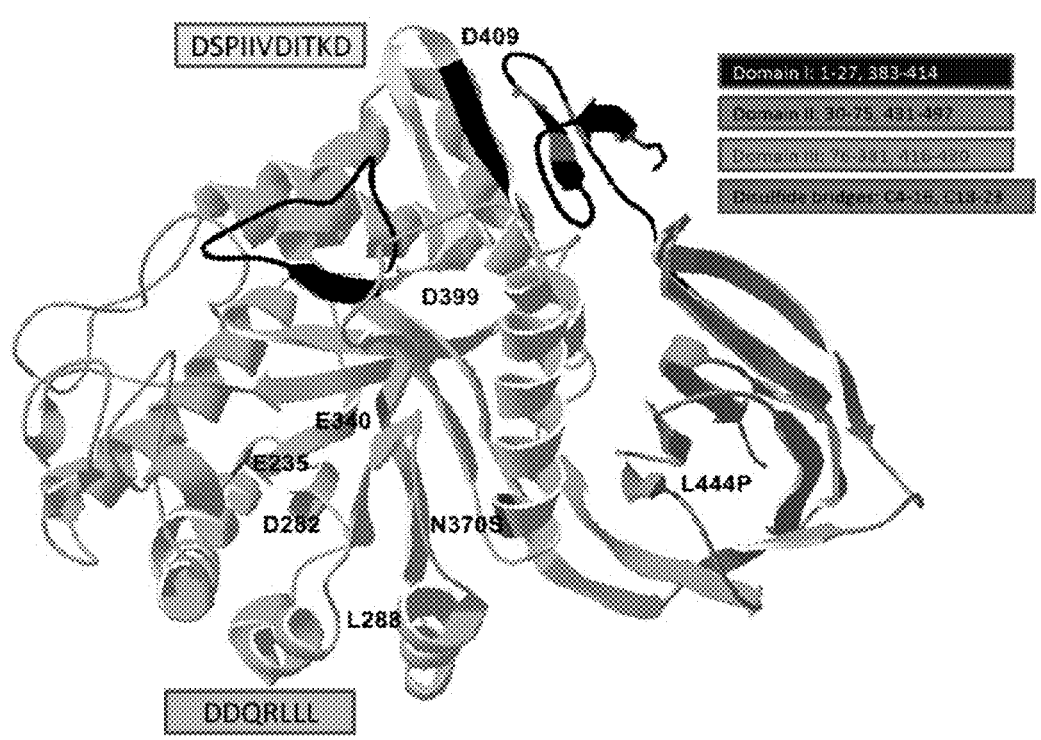
FIG. 4: Structure of WT GCase highlighting the potential ldLIMP2 binding sequence localization. The two amino acid sequences from FIG. 3 were mapped to the crystal structure of WT human GCase. The orientation of the sequences is indicated by the amino acid numbers in the highlighted (Yellow or Orange) regions. The domains of GCase are shown in various colors as are the disulfides. The potential ldLIMP2 binding (Yellow, D399 to D409) sequence forms a surface accessible loop in domain I. This sequence, DSPIIVDITKD (SEQ ID NO 3), and the DDQRLLL (SEQ ID NO 14) (Orange, D282 to L288 in Domain III) sequence are highly conserved in GCases from insects to humans. In red are the acid-base (E235) and nucleophile (E340) in catalysis, and N370S and L444P are common mutations causal to Gaucher disease.

The location of this GCase amino acid sequence is shown in a linear form in FIG. 3 (bracketed and in Orange highlight). This amino acid sequence is located in Domain I of the GCase crystal structure. Analysis of this region shows that the amino acids between N399 and D409 are surface exposed and form a structure that would be accessible for ligand binding to LIMP-2 (FIG. 3). However, amino acids F347-D398 and F411-H422 are more internal to the structure and less likely to be able to interact with LIMP-2. The likely exposed residues include the sequence DSPIIVDITKD (SEQ ID NO 3) (FIG. 4, in yellow). Searches of the databases for lysosomal glucocerebrosidases from multiple species show that this sequence is highly conserved and nearly invariant in mammals; the consensus sequence is DSPIIVDIAKD (SEQ ID NO 13). Based on these analyses, efforts were targeted to the amino acid sequence between D399 and D409 (FIG. 4). Although GCase is a membrane associated and not a transmembrane lysosomal protein, the mature GCase sequence does contain a di-leucine structure that has been previously identified as important in the indirect targeting of transmembrane proteins to the lysosome (55-57). This sequence spans amino acids D282-L288 (FIG. 3), DDQRLLL (SEQ ID NO 14) (FIG. 4) is also located in Domain III and was also analyzed for interactions/binding to LIMP-2 as a potential ligand sequence.

Figure 5:
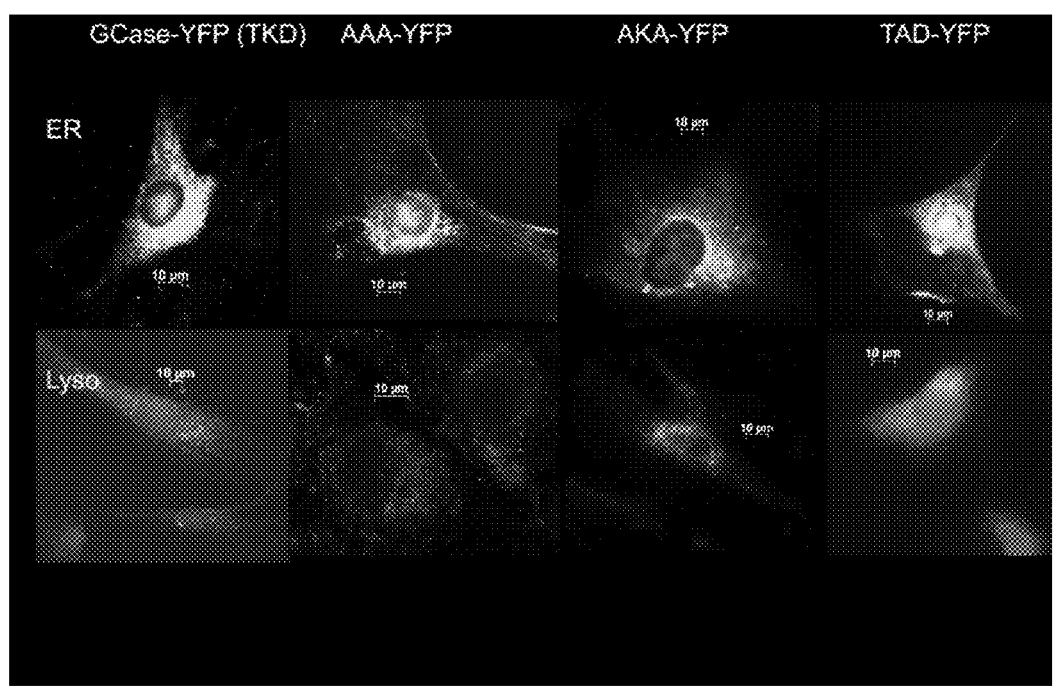
FIG. 5: Co-localization of GCases with specific alanine substitutions in the TKD sequence. GCase-YFP constructs were transfected into Gba1−/− fibroblasts and co-localization was evaluated with either calnexin or calreticulin (Green) for the ER/Golgi. The alanine (A) substitutions are as indicated in the WT TKD sequence. For the AAA and AKA GCases, the majority of the enzymes co-localized to the ER/Golgi (ER), whereas the AKD GCase showed about 50% of the enzyme localized to the lysosome (Lys).

LIMP-2 is a transmembrane protein whose cytoplasmic domain (ldLIMP-2) binds to and trafficks GCase to the lysosome (23). A series of alanine-swapped mutant proteins and peptides were made for cellular localization, immunoprecipitation, and secretion analyses. For the expression studies, Gba1 null/null fibroblasts were used and the GCase variant localized to cellular compartments. A 3 amino acid (TKD) and a 5 amino acid (DSPIIV (SEQ ID NO 15)) sequence of the complete 11 amino acid sequence of interest (FIG. 3) were targeted for alanine mutagenesis. The various mutant GCases for the TKD sequence showed immunofluorescence lysosomal localization (WT, AKA, TAD) to varying degrees or lack of this property (AAA), i.e., the AAA mutant showed no lysosomal localization, but abundant colocalization to the ER by using anti-calnexin/calreticulin. Thus, AAA was expressed in the cell, but was not trafficked to the lysosome. However, the WT and TAD mutant had similar ER and lysosomal localizations (FIG. 5). The AKA mutant showed less lysosomal localization compared to WT or the TAD mutant (FIG. 5).

To demonstrate a correlation between the colocalization results and LIMP-2 binding, the WT and variant GCases were expressed and purified by anti-GCase affinity chromatography, and used to conduct in vitro immunoprecipitation studies with ldLIMP-2 (FIG. 6). These results show that WT and the TAD GCases (FIGS. 6 A and D) were bound similarly by ldLIMP-2, whereas the AKA mutant (FIG. 6C) was much less bound and the AAA GCase did not bind to ldLIMP-2 (FIG. 6B). Quantitative densitometry results are shown in FIG. 6E. These results for ldLIMP-2 binding correlated well with the colocalization analyses, which followed a similar pattern for the WT, intermediate, or absent lysosomal localization.

Several additional peptides were used to explore the DSPIIVDITKD (SEQ ID NO 3) region by alanine scanning mutagenesis (Table 1) and a peptide from another region of GCase was used as a control. These peptides were synthesized with and without a fluorescent probe (FITC) covalently linked to the C terminal end to assess direct binding to ldLIMP-2 by changes in fluorescence polarization.

TABLE 1

Synthesized Peptides

| Sequence | location | M.W. (*FITC) | M.W. (non labeled) | Purity (%) |
|---|---|---|---|---|
| DSPIIV | 399-404 | 1032.2 | 642.8 | 95.3/98.0 |
| ASPIIV | 399-404 | 998.1 | 578.8 | 95.0/98.1 |
| DSPAIV | 399-404 | 990.1 | 600.7 | 96.5/98.2 |
| DSPIAV | 399-404 | 990.1 | 600.7 | 95.3/97.7 |
| DSPAAV | 399-404 | 948.1 | 514.6 | 95.4/95.1 |
| SKDVPL | 465-470 | 1047.2 | 657.8 | 96.6/98.0 |
| DDQRLLL | 282-288 | 1261.4 | 872 | 95.3/97.1 |
| ADQRLLL | 282-288 | 1226.4 | 828 | 96.1/97.5 |
| DAQRLLL | 282-288 | 1226.4 | 828 | 95.7/97.1 |
| DQQRAAA | 282-288 | 1144.2 | 745.8 | 95.9/98.0 |
| DPIARDL | 258-264 | 1247.4 | 849 | 95.1/97.5 |

Peptides were custom synthesized by American Peptide Company; QC: HPLC grade, purity: 95.1-98.896, MS analysis/desalted/lyophilized into powder.
Peptides were solubilized in Acetonitrile and further diluted in excessive water (>10000 fold) with sonication.
Product manufac. Number started from 35310 to 35316 and 35340 to 35346.

Figure 7A:
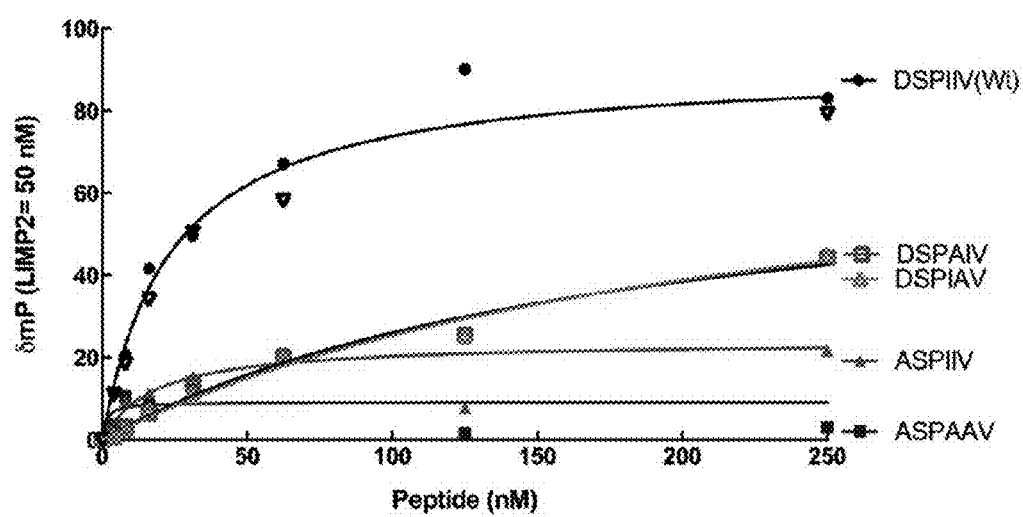

The interactions/binding of the GCase peptides, DSPIIV (SEQ ID NO 15) variants, to ldLIMP-2 are shown by the change in fluorescence polarization with increasing WT or mutant peptide concentration in the presence of a fixed amount of ldLIMP-2 (FIG. 7A). The substitution of an alanine for either of the isoleucines decreased binding to ldLIMP-2 by about 50%, whereas alanine substitution for the N-terminal aspartate nearly eliminated the binding to ldLIMP-2. Substitution of alanines for D399, I402 and I403 obliterated the binding.

Figure 7B:
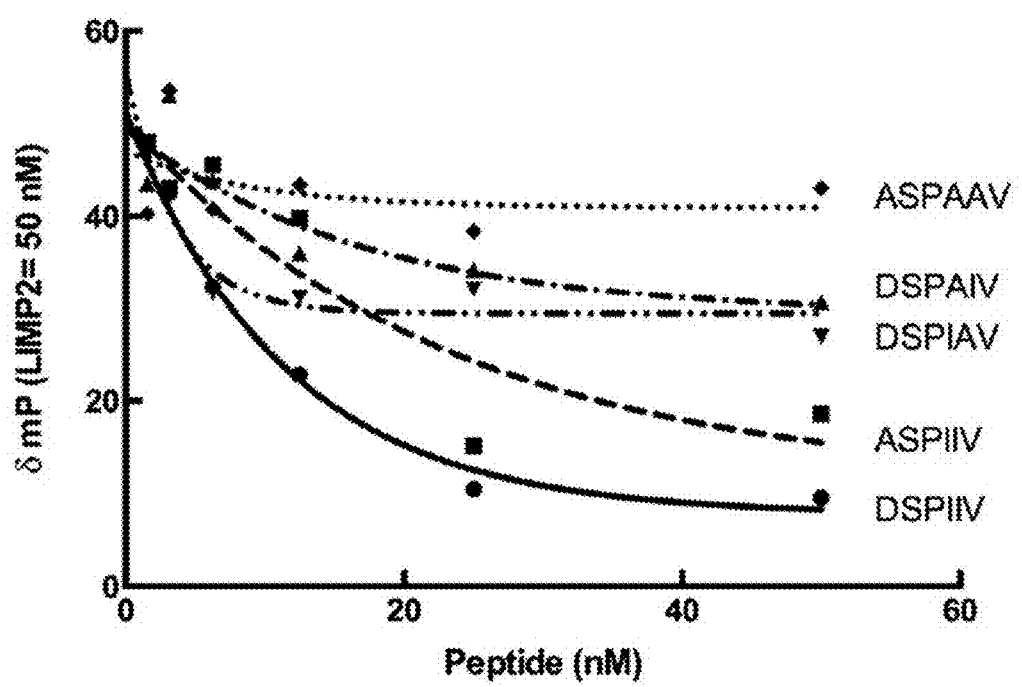
Figure 12:
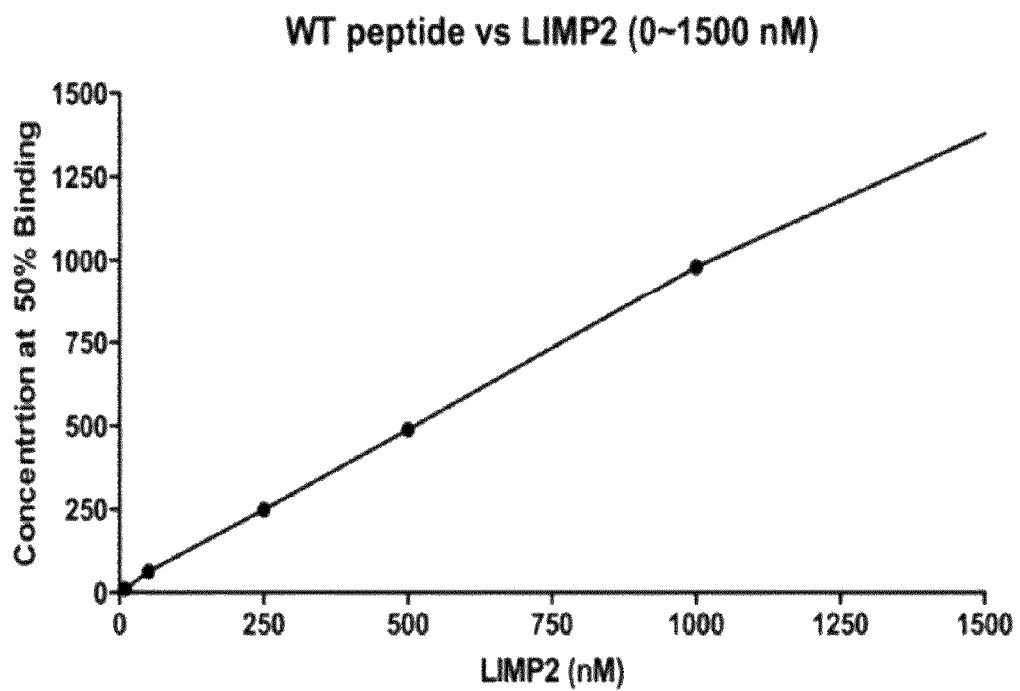
FIG. 12: Stoichiometry between ldLIMP2 and DSPIIV (SEQ ID NO 15). The peptide concentration giving 50% of maximal binding to ldLIMP2 (ordinate) and the concentration of ldLIMP2 (abscissa) have a 1:1 ratio. These results indicate a 1:1 stoichiometry and tight binding properties of DSPIIV (SEQ ID NO 15) and ldLIMP2.

To ensure that the fluorescent label was not interfering or promoting binding to ldLIMP-2, a similar experiment was conducted by addition of an unlabeled peptide to compete with the corresponding labeled peptide. The data show direct competition of the corresponding labeled and unlabeled peptides (FIG. 7B). Similarly, a direct comparison was conducted to assess the competition of either the labeled or unlabeled WT peptide for binding to ldLIMP-2 (FIG. 7C). The data show a symmetry of the change in fluorescence polarization that are nearly mirror images with either the labeled or unlabeled WT peptide in competition with ldLIMP-2. These data show that the fluorescent label did not alter the binding properties to ldLIMP-2. Using the WT labeled peptide the peptide binding to ldLIMP-2 was shown to have 1:1 stoichiometry and tight, i.e., the concentration of peptide needed for 50% binding to ldLIMP-2 was in a 1:1 molar correspondence (FIG. 12).

Figure 13A:
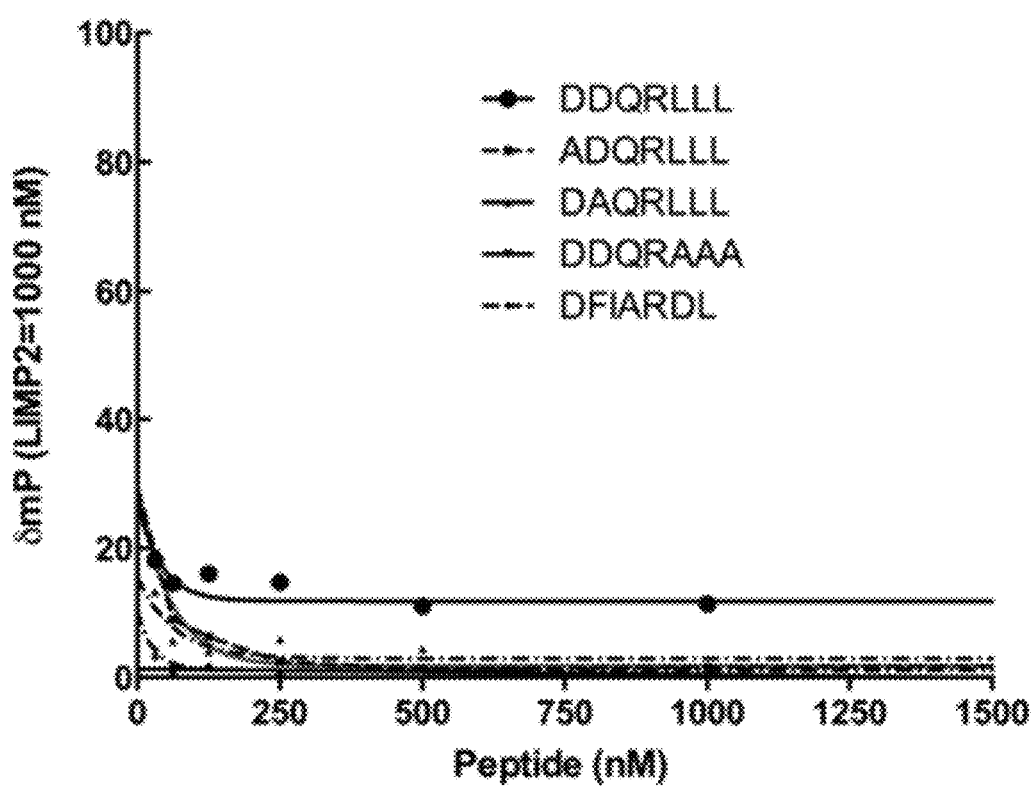
FIG. 13A-FIG. 13B: Competition and binding of fluorescent labeled or unlabeled DDQRLLL (SEQ ID NO 14) GCase peptides to ldLIMP2.
Figure 13B:
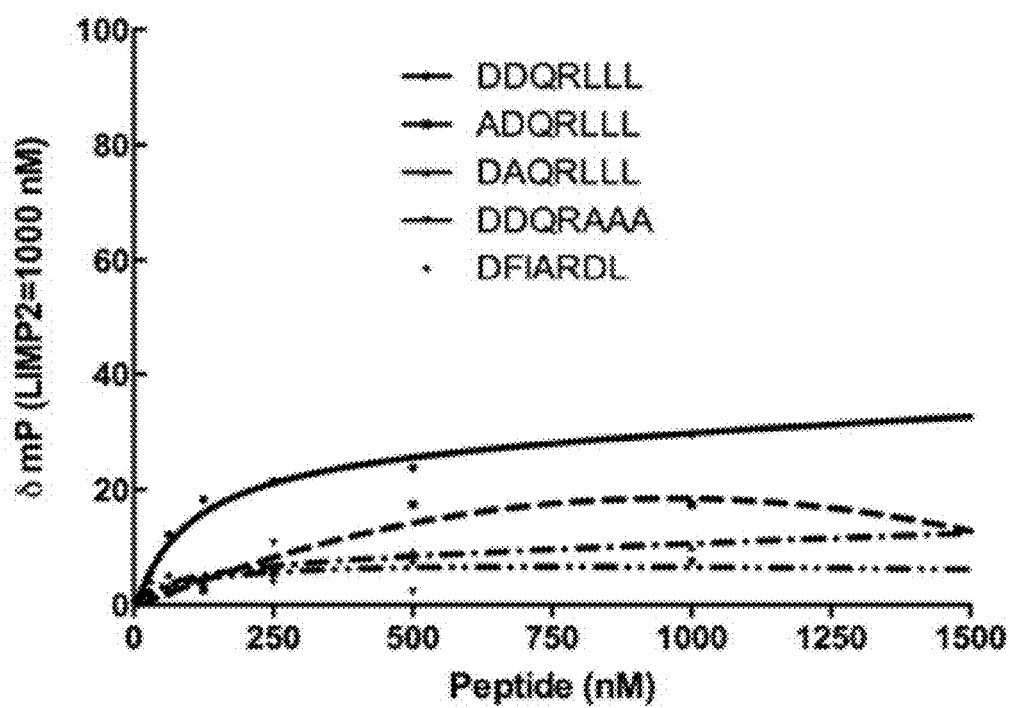

In other binding experiments, the DDQRLLL (SEQ ID NO 14) labeled and unlabeled peptides were synthesized and used. This peptide had little or no binding to LIMP-2 above background. Thus, the DDQRLLL (SEQ ID NO 14) had essentially no interaction with LIMP-2 (FIG. 13).

Figure 8A:
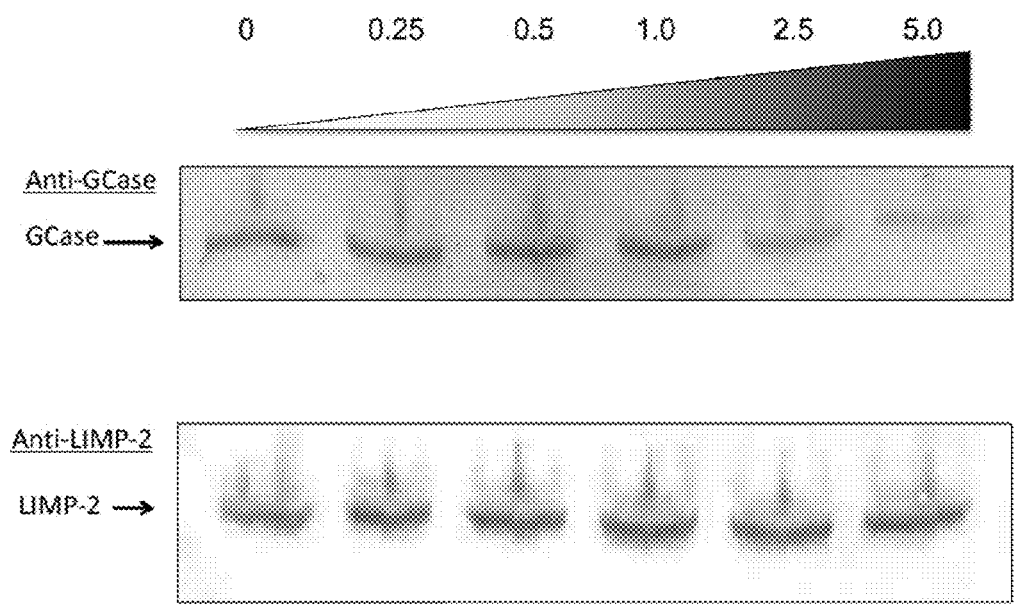
FIG. 8A-FIG. 8C: Immunoprecipitation of GCase in the presence of ldLIMP2 and increasing molar ratios of the WT (DSPIIV (SEQ ID NO 15)) peptide.
Figure 8B:
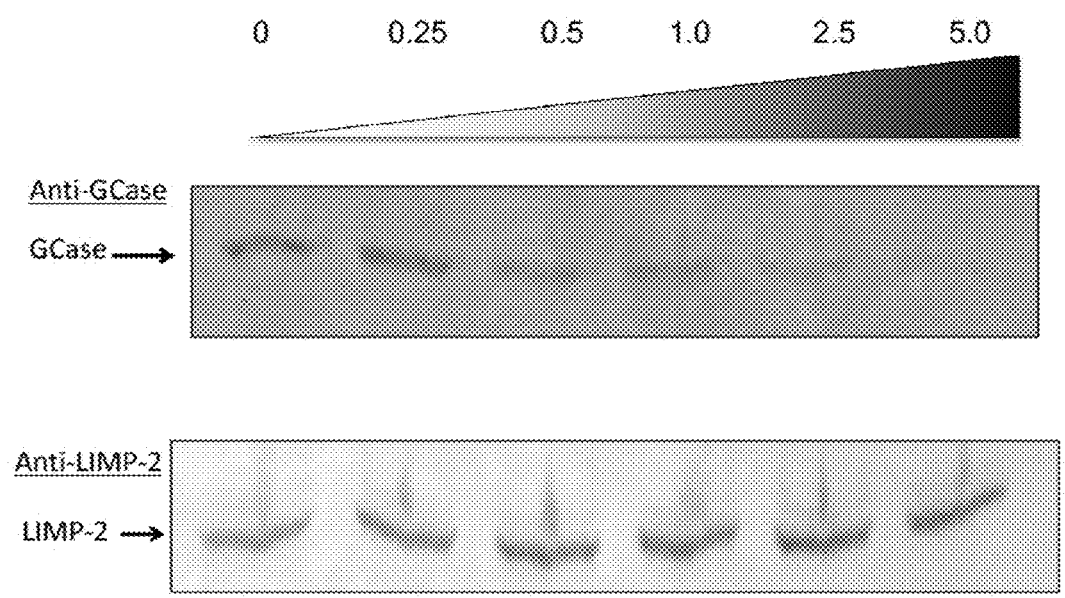
Figure 8C:
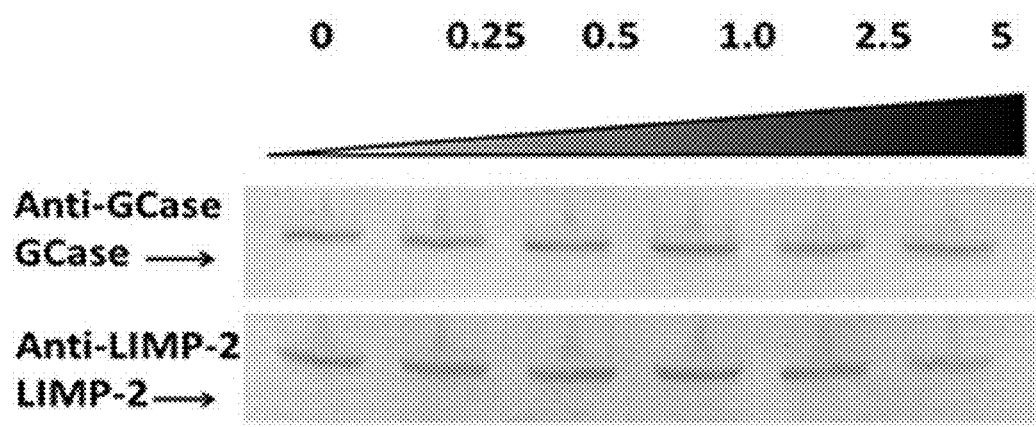

Immunoprecipitation and Competition Studies:

To further evaluate the interaction of ldLIMP-2, WT GCase, and the DSPIIV (SEQ ID NO 15) peptide, competitive immunoprecipitation experiments were conducted using increasing concentrations of the WT peptide in competition with GCase for binding (FIG. 8A). Increasing WT peptide, DSPIIV (SEQ ID NO 15), concentrations from 0 to 5× molar excess over GCase showed that the this peptide competes off binding to ldLIMP-2, when GCase was first incubated with LIMP-2 and then the WT peptide was added. A similar experiment was conducted in which the WT peptide was preincubated with ldLIMP-2 prior to adding purified GCase (FIG. 8B). Almost all GCase binding to LIMP2 was prevented at a 1 to 5× molar peptide ratios. The combined results (FIGS. 8A and B) show that the WT peptide can compete or prevent GCase binding to ldLIMP-2.

Figure 9:
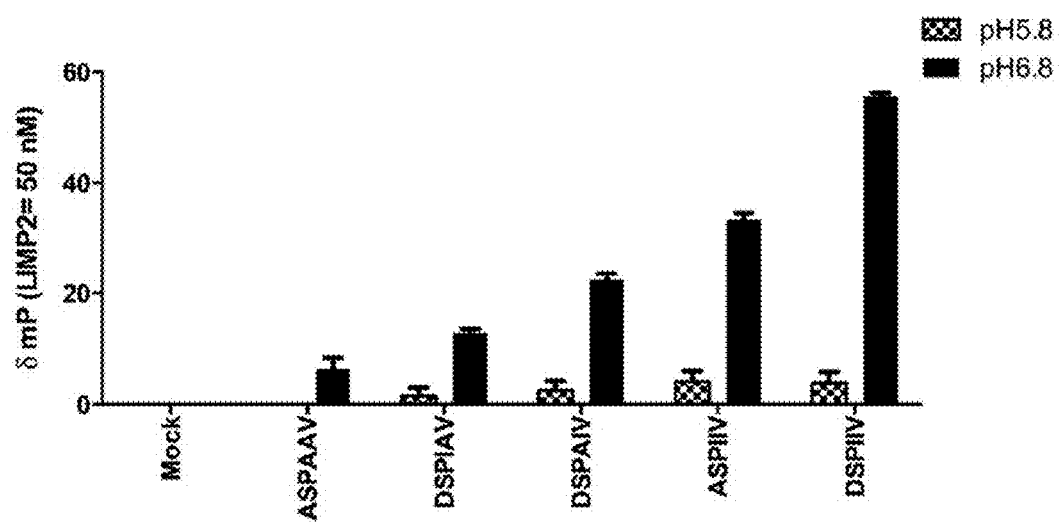
FIG. 9: Effect pH on binding WT and alanine substituted DSPIIV (SEQ ID NO 15) peptides to ldLIMP2. The binding of the different peptides to ldLIMP-2 showed little effect of alanine substitutions at pH-5.8. In comparison, incremental decreases were evident in ldLIMP2 binding at pH=6.8, the approximate pH of the ER/cis-Golgi, as follows: the triple mutant (ASPAAV) having the lowest binding (<10% of WT), the DSPAIV (SEQ ID NO 17) (I402A) and DSPIAV (SEQ ID NO 18) (I403A) mutants being intermediate (~40-50% of WT), and ASPIIV (SEQ ID NO 16) (D399A) having the least change (~50-60% of WT), relative to WT.
Figure 14A:
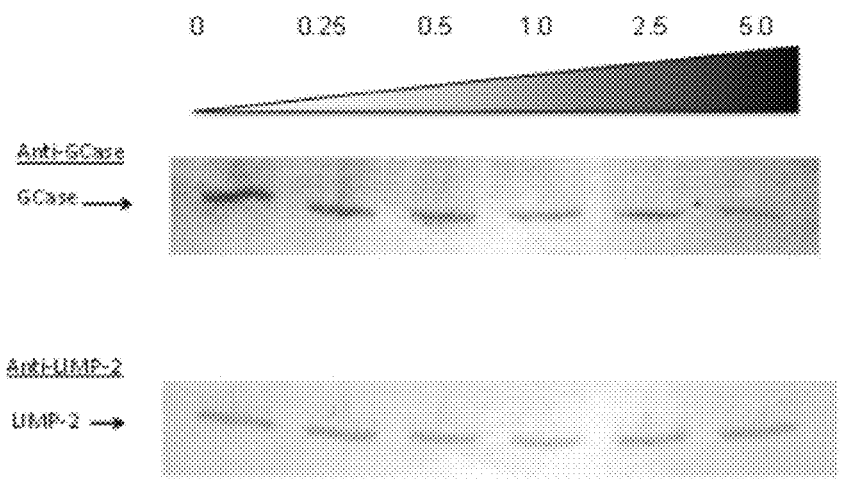
FIG. 14A-FIG. 14B: Immunoprecipitation of GCase in the presence of ldLIMP2 and increasing molar ratios of the WT (DDQRLLL (SEQ ID NO 14)) peptide.
Figure 14B:
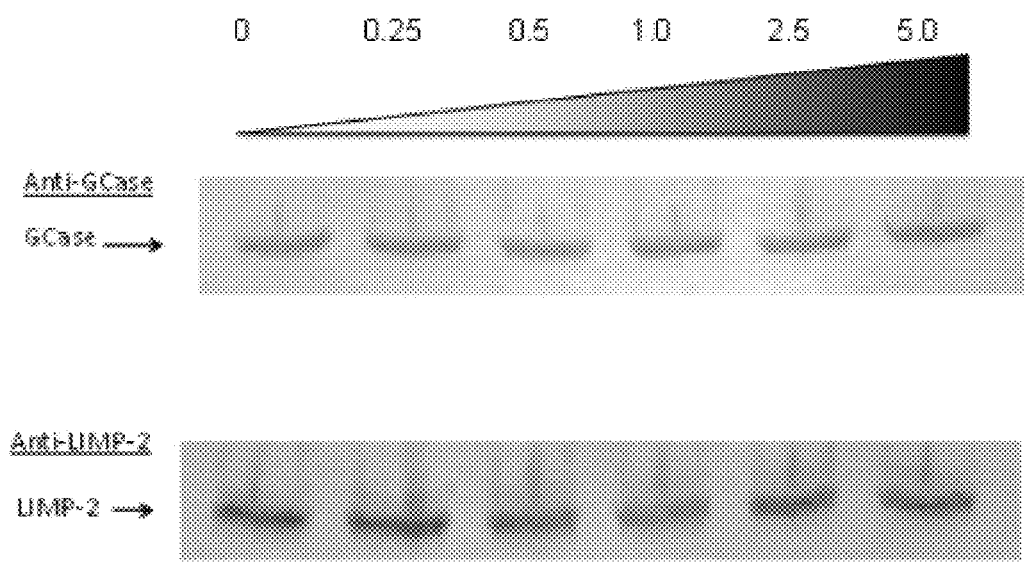

The DDQRLLL (SEQ ID NO 14) peptide from GCase was tested as a control. Although this sequence was contained in the GCase fragment (GCase-225) that did not localize to the lysosome, it does have a known motif for lysosomal targeting of transmembrane lysosomal proteins, which GCase is not. In addition, this sequence is highly conserved throughout phylogeny. Up to a 5× Molar excess this peptide does not compete with GCase for ldLIMP2 binding when the peptide was preincubated with LIMP-2 before GCase was added or when LIMP-2, the peptide and GCase were incubated together. FIGS. 14A and 14B.

pH-Dependency of ldLIMP-2/GCase Binding:

LIMP-2 binding to GCase is dependent upon pH in that greater binding is obtained at more neutral pH and dissociation obtains at pH 5.6 (23). The WT and various mutants of the DSPIIV (SEQ ID NO 15) peptide have differential pH dependency. Substitution of either isoleucine with alanine decreases the binding at pH 6.8 by 40-50%. The ASPIIV peptide (SEQ ID NO 16) binding was decreased by about 30-40%, whereas the ASPAAV peptide was decreased by ~90%. There is little effect on the binding at pH 5.8 of any of the peptides compared to WT (FIG. 9).

Figure 10A:
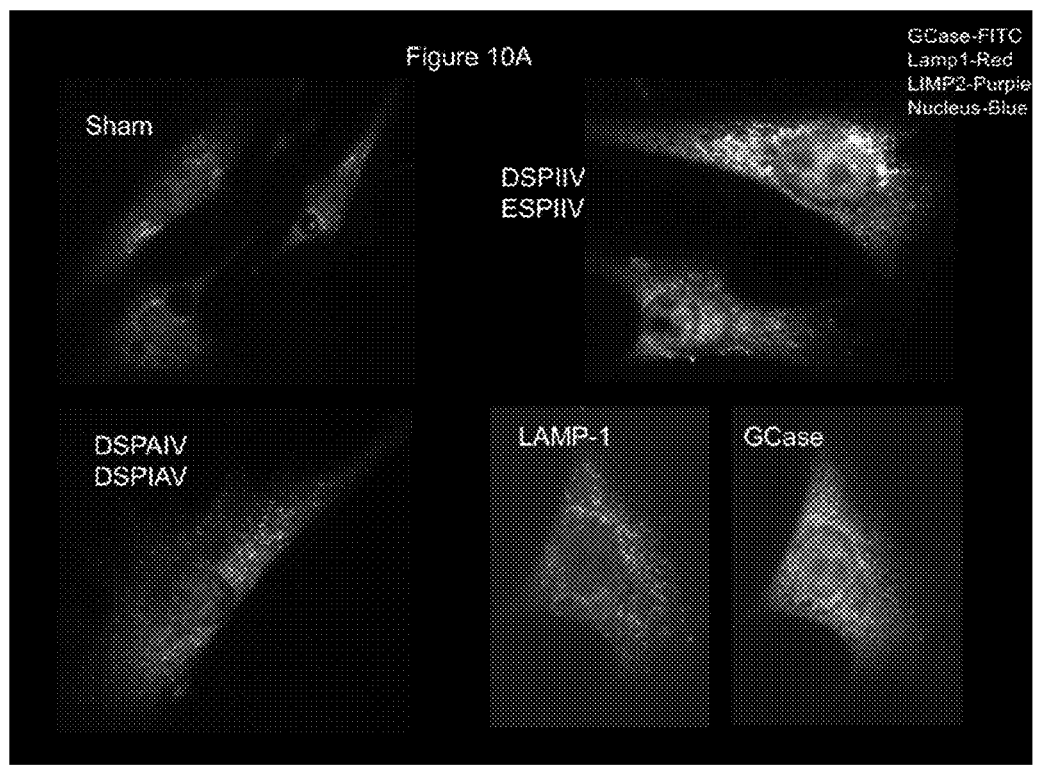
FIG. 10A-FIG. 10B: Intracellular localization of GCase DSPIIV (SEQ ID NO 15) variants in Gba1−/− cells.
Figure 10B:
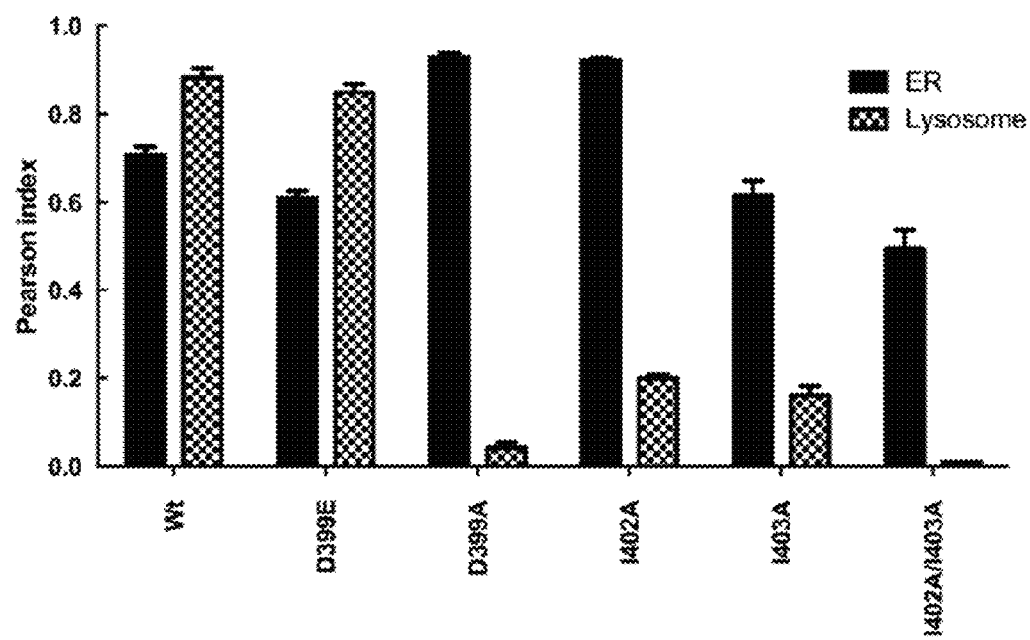

Effects of Mutations of DSPIIVDITKD (SEQ ID NO 3) on Cellular Colocalization and/or Secretion of GCase:

The effects on cellular localization of GCase from cells transfected with WT or various GCases with mutations in the target region are in FIG. 10A. Typical examples show that the WT or D399E GCases are targeted to the lysosomes indicating that the charge on amino acid 399 is important for this targeting. In comparison, the DSPAIV (SEQ ID NO 17) (I402A) or DSPIAV (SEQ ID NO 18) (I403A) do not localize to the lysosome. Essentially identical results were obtained with the ASPIIV (SEQ ID NO 16) (D399A) or 402A/I403A (double mutant) GCases. Confirmatory quantification by Pearson Indices of colocalization to the ER/Golgi or lysosome of all these expressed WT and mutant GCases are in FIG. 10B.

Figure 11A:
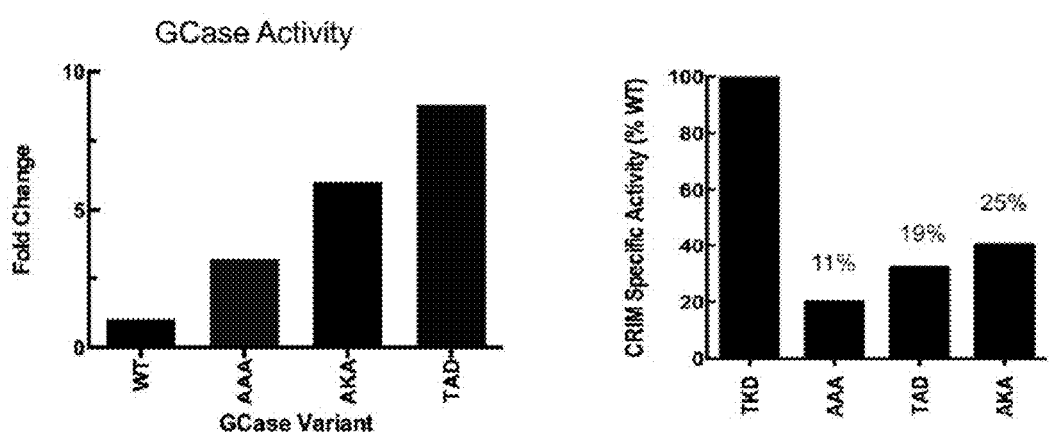
FIG. 11A-FIG. 11C: Secretion and retention of GCase with alanine variants in the TDK (FIG. 11A) or DSPIIV (SEQ ID NO 15) (FIG. 11B and FIG. 11C) sequences.
Figure 11B:
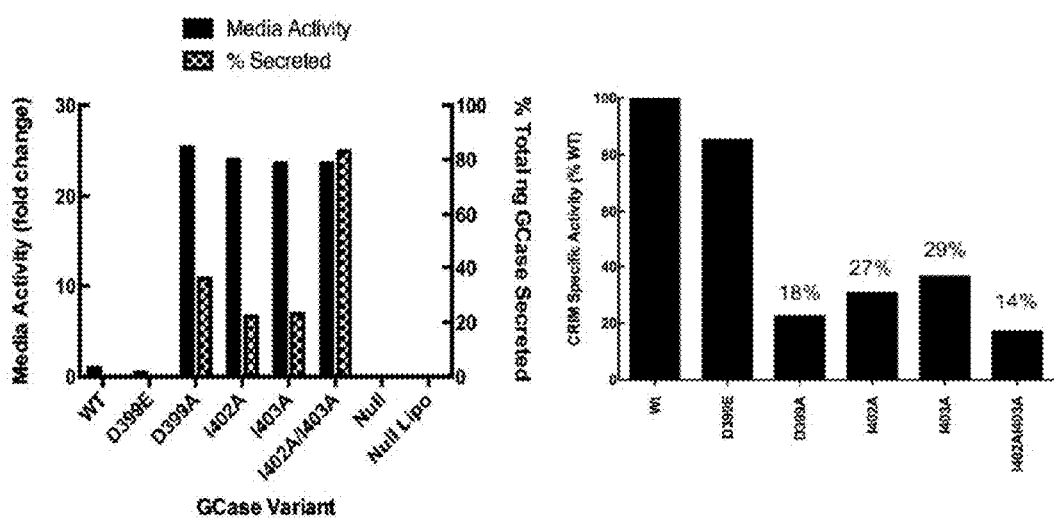
Figure 11C:
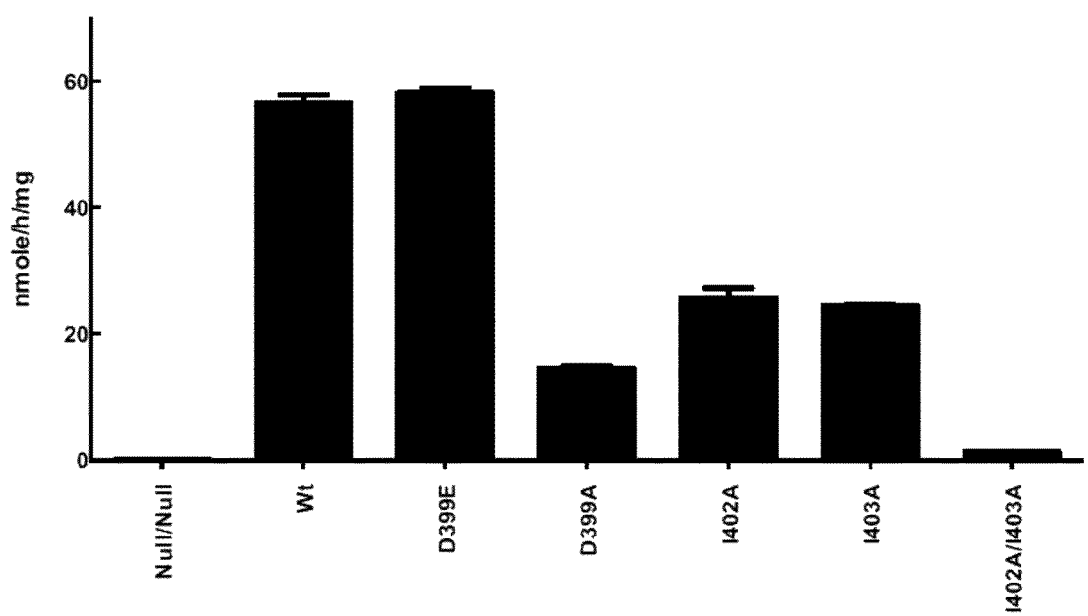

Corresponding effects on the secretion of GCases from the cells containing various mutations in DSPIIVDITDK were found by assessing the activity of GCases in the media and cell lysate (FIG. 11 A-C). Compared to the WT sequence (TDK), the amount of GCase activity in media progressively increased from the AAA to AKA to TAD mutants to about an 8-fold increase (FIG. 11A, left panel). The lower GCase activity in media of the AAA mutant seemed at odds with the lack of binding of this mutant to LIMP2 Immunoblots of the various mutations in the TKD sequence provided assessments of the GCase activity/amount of CRIM or CRIM specific activity, an estimate of the catalytic rate constant relative to WT enzyme. Using this assessment, the ratio of CRIM specific activities relative to WT (assigned 100%) for AAA, TAD, and AKA were 20%, 32%, and 49%, respectively (FIG. 11A, right panel), or that more GCase protein was required from the respective mutants to achieve the same enzyme activity as the WT. These results indicate that the levels of GCase protein secreted from the Gba1−/− fibroblasts were 2.5 to 5 fold greater than suggested by the enzyme activity measures and correspond well with the binding data (FIG. 6). Similarly for the DSPIIV sequence (SEQ ID NO 15), all of the alanine mutant GCases showed large increases (~25-fold) in media activity compared to WT, i.e., increased secretion of active GCase (FIG. 11B, left panel). When assessed for CRIM specific activity (CRIM SA) the alanine mutants had 14% to 29% of WT activity, implying that 7.1 (for the double mutant) to 3.4 (I403A) more GCase enzyme protein was secreted than suggested by the raw activity measures. The Gba1−/− cells transfected with the charge conserved substituted GCase, D399E, showed no media activity above background (i.e., zero) and a minor change in CRIM specific activity. Using the CRIM SA assessments and the total activities in lysates and media, the percent secreted GCase (ng) showed that ~83% of the I402A/I403A mutant was secreted from transfected cells. For the other mutants this ranged from 22-36%. This compares to ~0% for the WT or D399E GCases Immunoaffinity anti-GCase column purification of the various GCases from media confirmed the excesses of these mutant GCases and the inability to detect WT or D399E GCases in media (data not shown). Complementary data for the retention of GCases in cell lysates showed ~15-20% of WT or ESPIIV (D399E) activities with the single alanine mutants [ASPIIV (SEQ ID NO 16) (D399A), DSPAIV (SEQ ID NO 17) (I402A), and DSPIAV (SEQ ID NO 18) (I403A)], and <5% with the double DSPAAV (SEQ ID NO 19) (I402A/I403A) (FIG. 11C). Thus, all of the alanine mutated GCases that were shown to diminish ldLIMP-2 binding and poor lysosomal localization showed large increases in activity of GCase in the media, i.e., excess secretion.

TABLE 2

Proportion of GCase protein in cells and media

| GCase Variant | Cellular GCase (ng) | Media GCase (ng) | Total GCase (ng) | % Secreted |
|---|---|---|---|---|
| Human WT | 23 ± 4 | 0 | 23 ± 4 | 0 |
| D399A | 32 ± 4 | 18 ± 2 | 50 ± 4 | 36 |
| I402A | 38 ± 6 | 11 ± 4 | 49 ± 5 | 22 |
| I403A | 34 ± 2 | 10 ± 2 | 44 ± 3 | 23 |
| I402A/I403A | 4 ± 1 | 20 ± 3 | 24 ± 4 | 83 |
| Mouse WT | 64 ± 7 | 0 | 64 ± 7 | 0 |

Human WT and variant GCases were transfected into Gba1−/− cells with resultant transfection efficiencies of 20.5 ± 3%. The calculations were based on the specific activities of GCase relative to a standard curve of cross-reacting immunological material (CRIM) densities on immunoblots of purified human GCase, which has a specific activity of 1.1 nmole/hr/ng GCase. Cellular and Media GCase represent total ng from each source. Results are expressed as the mean ± SD, n = 3.

REFERENCES 1. deDuve, C. 1983. Lysosomes revisited. *Eur. J. Biochem.* 137:391.
2. Goldstein, J. L., Dana, S. E., Faust, J. R., Beaudet, A. L., and Brown, M. L. 1975. Role of lysosomal acid lipase in the metabolism of plasma low density lipoprotein. *J. Biol. Chem.* 250:8487-8795.
3. Horton, J. D., Goldstein, J. L., and Brown, M. S. 2002. SREBPs: activators of the complete program of cholesterol and fatty acid synthesis in the liver. *J Clin Invest* 109:1125-1131.
4. Varki, A., and Kornfeld, A. 1981. Lysosomal enzyme targeting: N-acetylglucosaminyl-phosphotransferase selectively phosphorylated native lysosomal enzymes. *J. Biol. Chem.* 256:11977-11980.
5. Kaplan, A., Achord, D. T., and Sly, W. S. 1977. Phosphohexosyl components of a lysosomal enzyme are recognized by pinocytosis receptors on human fibroblasts. *Proc. Natl. Acad. Sci. USA* 74:2026-2030.
6. Achord, D. T., Brot, F. E., Bell, C. E., and Sly, W. S. 1978. Human beta-glucuronidase: in vivo clearance and in vitro uptake by a glycoprotein recognition system on reticuloendothelial cells. *Cell* 15:269-278.
7. Kornfeld, S. a. S., W. 2001. I-Cell Disease and Pseudo-Hurler Polydystrophy: Disorders of Lysosomal Enzyme Phosphorylation and Localization. In *The Metabolic & Molecular Bases of Inherited Disease*. C. R. Scriver, Beaudet, A., Sly, W. and Valle, D., editor. New York: McGraw-Hill. 14.
8. Kornfeld, S. 1992. Structure and function of the mannose 6-phosphate/insulin like growth factor II receptors. *Annu. Rev. Biochem.* 61:307-330.
9. Barton, N. W., Brady, R. O., Dambrosia, J. M., Doppelt, S. H., Hill, S. C., Holder, C. A., Mankin, H. J., Murray, G. J., Zirzow, G. C., and Parker, R. I. 1992. Dose-dependent responses to macrophage-targeted glucocerebrosidase in a child with Gaucher disease. *J. Pediatr.* 120:277-280.
10. Grabowski, G. A., Saal, H., Wenstrup, R. J., and Barton, N. W. 1996. Gaucher disease: A prototype for molecular medicine. *Crit. Rev. Hem. Onco.* 23:25-55.
11. Desnick, R. J., and Bishop, D. F. 1989. Fabry disease: alpha-galactosidase deficiency; Schindler disease: alpha-N-Acetylgalactosaminidase deficiency. In *The Metabolic Basis of Inherited Disease*. C. R. Scriver, A. L. Beaudet, W. S. Sly, and D. Valle, editors. New York: McGraw-Hill. 1751-1796.
12. Desnick, R. J., Ioannou, Y. A. and Eng, C. M. 2001. α-Galactosidase A Deficiency: Fabry Disease. In *The Metabolic & Molecular Bases of Inherited Disease*. C. R. Scriver, Beaudet, A., Sly, W. and Valle, D., editor. New York: McGraw-Hill. 3733-3774.
13. Leonova, T., and Grabowski, G. A. 2000. Fate and sorting of acid beta-glucosidase in transgenic mammalian cells. *Mol. Genet. Metab.* 70:281-294.
14. Brady R O, Kanfer J N, Bradley R M, and Shapiro D. Demonstration of a deficiency of glucocerebroside-cleaving enzyme in Gaucher's disease. *Journal of Clinical Investigation*. 1966; 45 (1112-5.
15. Brady R O, Kanfer J N, and Shapiro D. Metabolism of glucocerebrosides. II. Evidence of an enzymatic deficiency in Gaucher's disease. *Biochem Biophys Res Commun.* 1965; 18(221-5.
16. Grabowski G A, Petsko, G. A., Kolodny, E. In: Valle D, Beaudet, A. L., Vogelstein, B., Kinzler, K. W., Antonarakis, S. E., Ballabio, A., Sly, W. S. ed. *The Metabolic and Molecular Bases of Inherited Disease*. New York: McGraw-Hill; 2010:On-line.
17. Grabowski G A, Kolodny, E. H., Weinreb, N. J., Rosenbloom, B. E., Prakash-Cheng, A., Kaplan, P., Charrow, J., Pastores, G. M., Mistry, P. K. In: Scriver C, Beaudet, A., Sly, W., and Valle, D. ed. *The Metabolic and Molecular Bases of Inherited Diseases*. New York: McGraw-Hill; 2006:genetics.accessmedicine.com.
18. Liou B, Kazimierczuk A, Zhang M, Scott C R, Hegde R S, and Grabowski G A. Analyses of variant acid beta-glucosidases: effects of Gaucher disease mutations. *The Journal of biological chemistry.* 2006; 281(7):4242-53.
19. Sorge J, West C, Westwood B, and Beutler E. Molecular cloning and nucleotide sequence of the human glucocerebrosidase gene. *Proc Natl Acad Sci USA.* 1985; 82(7289-93.
20. Berg-Fussman A, Grace M E, Ioannou Y, and Grabowski G A. Human b-glucosidase: N-glycosylation site occupancy and the effect of glycosylation on enzymatic activity. *J Biol Chem.* 1993; 268(14861-6.

21. Kornfeld SaS, W. In: Scriver C R, Beaudet, A., Sly, W. and Valle, D. ed. The *Metabolic & Molecular Bases of Inherited Disease*. New York: McGraw-Hill; 2001:14.
22. Varki A, and Kornfeld A. Lysosomal enzyme targeting: N-acetylglucosaminyl-phosphotransferase selectively phosphorylated native lysosomal enzymes. *J Biol Chem*. 1981; 256(11977-80.
23. Reczek D, Schwake M, Schroder J, Hughes H, Blanz J, Jin X, Brondyk W, Van Patten S, Edmunds T, and Saftig P. LIMP-2 is a receptor for lysosomal mannose-6-phosphate-independent targeting of beta-glucocerebrosidase. *Cell*. 2007; 131(4):770-83.
24. Leonova T, and Grabowski G A. Fate and sorting of acid beta-glucosidase in transgenic mammalian cells. *Mol Genet Metab*. 2000; 70(4):281-94.
25. Saftig P, Schroder B, and Blanz J. Lysosomal membrane proteins: life between acid and neutral conditions. *Biochemical Society transactions*. 2010; 38(6):1420-3.
26. Saftig P, and Klumperman J. Lysosome biogenesis and lysosomal membrane proteins: trafficking meets function. *Nature reviews Molecular cell biology*. 2009; 10(9):623-35.
27. Ogata S, and Fukuda M. Lysosomal targeting of Limp II membrane glycoprotein requires a novel Leu-Ile motif at a particular position in its cytoplasmic tail. *The Journal of biological chemistry*. 1994; 269(7):5210-7.
28. Zachos C, Blanz J, Saftig P, and Schwake M. A critical histidine residue within LIMP-2 mediates pH sensitive binding to its ligand beta-glucocerebrosidase. *Traffic*. 2012; 13(8):1113-23.
29. Wang X, Peng W, Ren J, Hu Z, Xu J, Lou Z, Li X, Yin W, Shen X, Porta C, et al. A sensor-adaptor mechanism for enterovirus uncoating from structures of EV71. *Nature structural & molecular biology*. 2012; 19(4):424-9.
30. Chen P, Song Z, Qi Y, Feng X, Xu N, Sun Y, Wu X, Yao X, Mao Q, Li X, et al. Molecular determinants of enterovirus 71 viral entry: cleft around GLN-172 on VP1 protein interacts with variable region on scavenge receptor B 2. *The Journal of biological chemistry*. 2012; 287(9):6406-20.
31. Yamayoshi S, and Koike S. Identification of a human SCARB2 region that is important for enterovirus 71 binding and infection. *Journal of virology*. 2011; 85(10):4937-46.
32. Yamayoshi S, Yamashita Y, Li J, Hanagata N, Minowa T, Takemura T, and Koike S. Scavenger receptor B2 is a cellular receptor for enterovirus 71. *Nature medicine*. 2009; 15(7):798-801.
33. Knipper M, Claussen C, Ruttiger L, Zimmermann U, Lullmann-Rauch R, Eskelinen E L, Schroder J, Schwake M, and Saftig P. Deafness in LIMP2-deficient mice due to early loss of the potassium channel KCNQ1/KCNE1 in marginal cells of the stria vascularis. *The Journal of physiology*. 2006; 576(Pt 1):73-86.
34. Blanz J, Groth J, Zachos C, Wehling C, Saftig P, and Schwake M. Disease-causing mutations within the lysosomal integral membrane protein type 2 (LIMP-2) reveal the nature of binding to its ligand beta-glucocerebrosidase. *Hum Mol Genet*. 2010; 19(4):563-72.
35. Maniwang E, Tayebi N, and Sidransky E. Is Parkinson disease associated with lysosomal integral membrane protein type-2?: challenges in interpreting association data. *Molecular genetics and metabolism*. 2013; 108(4):269-71.
36. Lopez G, and Sidransky E. Predicting parkinsonism: new opportunities from Gaucher disease. *Molecular genetics and metabolism*. 2013; 109(3):235-6.
37. Westbroek W, Gustafson A M, and Sidransky E. Exploring the link between glucocerebrosidase mutations and parkinsonism. *Trends in molecular medicine*. 2011; 17(9):485-93.
38. Cullen V, Sardi S P, Ng J, Xu Y H, Sun Y, Tomlinson J J, Kolodziej P, Kahn I, Saftig P, Woulfe J, et al. Acid beta-glucosidase mutants linked to Gaucher disease, Parkinson disease, and Lewy body dementia alter alpha-synuclein processing. *Ann Neurol*. 2011; 69(6):940-53.
39. Sidransky E, Nails M A, Aasly J O, Aharon-Peretz J, Annesi G, Barbosa E R, Bar-Shira A, Berg D, Bras J, Brice A, et al. Multicenter analysis of glucocerebrosidase mutations in Parkinson's disease. *The New England journal of medicine*. 2009; 361(17):1651-61.
40. Mazzulli J R, Xu Y H, Sun Y, Knight A L, McLean P J, Caldwell G A, Sidransky E, Grabowski G A, and Krainc D. Gaucher disease glucocerebrosidase and alpha-synuclein form a bidirectional pathogenic loop in synucleinopathies. *Cell*. 2011; 146(1):37-52.
41. Sidransky, E. 2005. Gaucher disease and parkinsonism. *Mol Genet Metab* 84:302-304
42. Nichols, W. C., Pankratz, N., Marek, D. K., Pauciulo, M. W., Elsaesser, V. E., Halter, C. A., Rudolph, A., Wojcieszek, J., Pfeiffer, R. F., and Foroud, T. 2009. Mutations in GBA are associated with familial Parkinson disease susceptibility and age at onset. *Neurology* 72:310-316.
43. Mullin N P, Hitchen P G, and Taylor M E. Mechanism of $Ca^{2+}$ and monosaccharide binding to a C-type carbohydrate-recognition domain of the macrophage mannose receptor. *J Biol Chem*. 1997; 272(5668-81.
44. Ezkowitz A B, Sastry K, Bailly P, and Warner A. Molecular characterization of the human macrophage mannose receptor: Demonstration of multiple carbohydrate recognition-like domains and phagocytosis of yeasts in Cos-1 cells. *J Exp Med*. 1990; 172(1785-94.
45. Kornfeld S. Structure and function of the mannose 6-phosphate/insulin like growth factor II receptors. *Annu Rev Biochem*. 1992; 61(307-30.
46. Velayati A, DePaolo J, Gupta N, Choi J H, Moaven N, Westbroek W, Goker-Alpan O, Goldin E, Stubblefield B K, Kolodny E, et al. A mutation in SCARB2 is a modifier in Gaucher disease. *Human mutation*. 2011; 32(11):1232-8.
47. Sun Y, Qi X, and Grabowski G A. Saposin C is required for normal resistance of acid beta-glucosidase to proteolytic degradation. *J Biol Chem*. 2003; 278(34):31918-23
52. Edgar R C. MUSCLE: multiple sequence alignment with high accuracy and high throughput. *Nucleic Acids Res*. 2004; 32(5):1792-7.
53. Edgar R C. MUSCLE: a multiple sequence alignment method with reduced time and space complexity. *BMC bioinformatics*. 2004; 5(113.
54. Liou B, and Grabowski G A. Is E326K glucocerebrosidase a polymorphic or pathological variant? *Molecular genetics and metabolism*. 2012; 105(3):528-9.
55. Misra S, Puertollano R, Kato Y, Bonifacino J S, and Hurley J H. Structural basis for acidic-cluster-dileucine sorting-signal recognition by VHS domains. *Nature*. 2002; 415(6874):933-7.

56. Gough N R, Zweifel M E, Martinez-Augustin O, Aguilar R C, Bonifacino J S, and Fambrough D M. Utilization of the indirect lysosome targeting pathway by lysosome-associated membrane proteins (LAMPs) is influenced largely by the C-terminal residue of their GYXXphi targeting signals. *J Cell Science.* 1999; 112(4257-69.
57. Barriocanal J G, Bonifacino J S, Yuan L, and Sandoval I V. Biosynthesis, glycosylation, movement throught the golgi system and transport to lysosomes by N-linked carbohydrate independent mechanism of three lysosomal integral membrane proteins. *J Biol Chem.* 1986; 261 (1604-7.
48. Bultron G, Kacena K, Pearson D, Boxer M, Yang R, Sathe S, Pastores G, and Mistry P K. The risk of Parkinson's disease in type 1 Gaucher disease. *Journal of inherited metabolic disease.* 2010; 33(2):167-73.
49. Sardi S P, Clarke J, Viel C, Chan M, Tamsett T J, Treleaven C M, Bu J, Sweet L, Passini M A, Dodge J C, et al. Augmenting CNS glucocerebrosidase activity as a therapeutic strategy for parkinsonism and other Gaucher-related synucleinopathies. *Proc Natl Acad Sci USA.* 2013; 110(9):3537-42.
50. Sardi S P, Singh P, Cheng S H, Shihabuddin L S, and Schlossmacher M G. Mutant GBA1 expression and synucleinopathy risk: first insights from cellular and mouse models. *Neuro-degenerative diseases.* 2012; 10(1-4):195-202.
51. Sardi S P, Clarke J, Kinnecom C, Tamsett T J, Li L, Stanek L M, Passini M A, Grabowski G A, Schlossmacher M G, Sidman R L, et al. CNS expression of glucocerebrosidase corrects alpha-synuclein pathology and memory in a mouse model of Gaucher-related synucleinopathy. *Proc Natl Acad Sci USA.* 2011; 108(29):12101-6.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

To the extent dimensions and values are disclosed herein, such are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A glucocerebrosidase (GCase) comprising at least 85% sequence identity to human GCase amino acid sequence as set forth in SEQ ID NO: 2 comprising one or more mutations at a position selected from 397, 399, 400, 401, 402, 403, 407, 408, 409, and combinations thereof, wherein said mutation decreases LIMP-2 binding, wherein the residues at positions 399-403 with reference to SEQ ID NO: 2 comprise a sequence selected from ASPII (SEQ ID NO: 7), DSAII (SEQ ID NO: 8), DSPAI (SEQ ID NO: 9), DSPIA (SEQ ID NO: 10), ASPIA (SEQ ID NO: 11), ASPAA (SEQ ID NO: 12), ESAII (SEQ ID NO: 21), ESPAI (SEQ ID NO: 22), ESPIA (SEQ ID NO: 23), and wherein said GCase protein at position 407-409 of SEQ ID NO: 2 comprises a sequence selected from AAA, AKA, TAD, and TAE.

2. The GCase protein of claim 1, wherein said mutation substantially ablates LIMP-2 binding.

3. The GCase protein of claim 1, wherein said mutation changes the charge at said position.

4. The GCase protein of claim 1, wherein said mutation changes the charge at said position to a positive charge.

5. The GCase protein of claim 1, wherein said mutation changes the amino acid at said position to an amino acid selected from alanine and glycine.

6. The GCase protein of claim 1, wherein said position is selected from 399, 402, 403, 407, 408, 409, and a combination thereof.

7. The GCase protein of claim 1, wherein said position is selected from 399, 402, 403, and a combination thereof.

8. The GCase protein of claim 1, wherein said position is selected from 407, 408, 409, and a combination thereof.

9. The GCase protein of claim 1, wherein said mutation decreases localization of said recombinant protein to the lysosomes of a cell while it is synthesized.

10. The GCase protein of claim 1, wherein said GCase protein has biological activity that is substantially equivalent to the wild type GCase biological activity.

11. The GCase protein of claim 1, wherein said GCase protein has enzymatic activity that is substantially equivalent to the wild type GCase biological activity.

12. The GCase protein of claim 1, wherein said GCase protein is capable of being taken up into cells via non-LIMP-2 mechanisms in substantially the same manner as wild type GCase.

13. The GCase protein of claim 1, wherein said GCase protein further comprises additional N-terminal and/or C-terminal amino acids.

14. The GCase protein of claim 1, wherein said mutation increases secretion of said GCase protein from cells in which it is synthesized.

15. The GCase protein of claim 1, comprising a mutation selected from D399E, D405E, D409E, and combinations thereof.

* * * * *